(12) United States Patent
Liu et al.

(10) Patent No.: US 8,957,374 B2
(45) Date of Patent: Feb. 17, 2015

(54) SYSTEMS AND METHODS FOR MEASURING BIREFRINGENCE IN GLASS AND GLASS-CERAMICS

(71) Applicant: Corning Incorporated, Corning, NY (US)

(72) Inventors: Anping Liu, Horseheads, NY (US); Rostislav Vatchev Roussev, Painted Post, NY (US); Vitor Marino Schneider, Painted Post, NY (US); Alana Marie Whittier, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/033,954

(22) Filed: Sep. 23, 2013

(65) Prior Publication Data

US 2014/0092377 A1 Apr. 3, 2014

Related U.S. Application Data

(60) Provisional application No. 61/706,891, filed on Sep. 28, 2012.

(51) Int. Cl.
*G01J 5/00* (2006.01)
*G01N 21/23* (2006.01)
*G01J 4/04* (2006.01)

(52) U.S. Cl.
CPC .. *G01N 21/23* (2013.01); *G01J 4/04* (2013.01)
USPC .................................................. 250/338.1

(58) Field of Classification Search
CPC ............. G02B 27/4261; G02B 5/1819; G02B 5/3066; G02B 6/126
See application file for complete search history.

(56) References Cited

U.S. PATENT DOCUMENTS

| | | | |
|---|---|---|---|
| 3,286,581 A | 11/1966 | Acloque et al. | 88/14 |
| 4,353,649 A | 10/1982 | Kishii | 356/33 |
| 4,655,589 A | 4/1987 | Cestaro et al. | 356/35 |
| 5,164,589 A | 11/1992 | Sjodin | 250/227.24 |

(Continued)

FOREIGN PATENT DOCUMENTS

| | | |
|---|---|---|
| GB | 827288 | 2/1960 |
| JP | 11281501 A | 10/1999 |
| WO | WO2012128184 A1 | 9/2012 |

OTHER PUBLICATIONS

Mehan et al., "Optical waveguiding and birefringence properties of sputtered zinc oxide (ZnO) thin films on glass," 2004, Optical Materials, pp. 241-248.*

(Continued)

*Primary Examiner* — Kiho Kim
(74) *Attorney, Agent, or Firm* — Jason A. Barron

(57) ABSTRACT

Systems and methods of for measuring birefringence and stress in a sample made of ion-exchanged glass or a ceramic are disclosed, wherein the method includes digitally capturing TE and TM angular spectra of intensity versus pixel number for the sample. The TE and TM angular spectra are processed to minimize differences between respective regions of the TE and TM angular spectra. The amount of shift in pixels that best overlaps the processed TE and TM spectra is determined. The birefringence B is calculated by multiplying the pixel shift by the index resolution. The stress is calculated by multiplying the birefringence by the stress-optic coefficient.

21 Claims, 17 Drawing Sheets

(56) References Cited

U.S. PATENT DOCUMENTS

| | | | |
|---|---|---|---|
| 7,206,470 B2* | 4/2007 | Li et al. | 385/14 |
| 7,602,474 B2* | 10/2009 | Mori et al. | 355/71 |
| 2011/0001965 A1 | 1/2011 | Messerschmidt | 356/317 |

OTHER PUBLICATIONS

W. Snyder and J. D. Love, "the Goos-Hänchen shift", Appl. Opt. 15, pp. 236-238 (1976).

Anna Samoc et al., "Prism coupler and microscopic investigations of DNA films," Sep. 5, 2007, vol. 6646, pp. 664607 1-9.

Hao Yu[a], et al., "Alkyl-substituted carboxyl-containing polyaryletherketones and the crosslinking modifications with various bisphenols: Preparation and optical properties," Jun. 24, 2010, vol. 51, No. 14, pp. 3269-3276.

Ping-Rang Hua et al., "Shallow Ti:LiNbO$_3$ Strip Waveguide," IEEE Photonics Journal, Apr. 1, 2012, vol. 4, No. 2, pp. 520-527.

PCT/US2013/061652, "Search Report and Written Opinion," pp. 1-14, issued on Feb. 18, 2014.

\* cited by examiner

SYSTEMS AND METHODS FOR MEASURING BIREFRINGENCE IN GLASS AND GLASS-CERAMICS

CROSS REFERENCE TO RELATED APPLICATIONS

This application claims the benefit of priority under 35 U.S.C. § of U.S. Provisional Application Ser. No. 61/706,891, filed on 28 Sep. 2012, the contents of which are relied upon and incorporated herein by reference in their entirety as if fully set forth below.

FIELD

The present disclosure relates to measuring birefringence, and in particular to systems and methods for measuring birefringence in certain types of glass and ceramics that have relatively high attenuation, as well as in glass and ceramics that have a decrease in refractive index near the surface.

BACKGROUND

Certain types of glasses and glass-ceramics can be chemically strengthened by an ion exchange process that may change the surface refractive index of the material. The strengthening is due to the formation of a near-surface compression layer that usually creates birefringence.

With the increased use of chemically strengthened glasses and glass-ceramics in such products as smart phones, computer screens and flat-panel televisions, there is an increasing need for nondestructive, high-throughput measurements of the surface stress for quality control during manufacturing.

A nondestructive prism-coupling-based method for characterization of the stress profile is currently used for chemically strengthened glasses in which the ion-exchange process results in an increase in the surface refractive index and thus the formation of an optical waveguide. The method is based on index-profile recovery for two orthogonal polarizations of visible-wavelength light based on measurements of the transverse-electric (TE) and transverse-magnetic (TM) guided mode spectra. The difference in the two index profiles (namely, in the depth distribution of birefringence) is approximately linearly related to the depth distribution of stress via the stress-optic coefficient (SOC).

Another prism-coupling-based method is used for measuring the surface refractive index of transparent substrates with a typical precision of ±0.0002 RIU (refractive index units). The method scans a laser beam over a range of angles at the prism-sample interface. If used to measure surface birefringence and stress, the method would produce a birefringence error of ±0.0003 RIU based on the summation rule for two random errors, one for each polarization measurement. Since the typical SOC of common chemically strengthened glasses is on the order of $3 \times 10^{-6}$ RIU/MPa, the resulting stress-measurement error would be about 100 MPa. This is too large for most practical applications, where the typical surface stresses are on the order of 200-900 MPa. A measurement error below 5% is usually needed for process and quality control during manufacturing. In addition, the scanning used in this approach is time-consuming and results in slow measurements, which is not ideal for performing quality control in a commercial setting.

Another problem with conventional coupling prism-based stress measurement methods and systems is that they are not capable of making accurate measurements of surface stress in ion-exchange glasses with either a decreased surface refractive index or a high attenuation.

SUMMARY

The present disclosure relates to nondestructive high-throughput measurements of surface or near-surface birefringence, and surface or near-surface stress in glass and glass-ceramics. The glass or glass-ceramics may be opaque due to significant optical absorption, significant light scattering, or both.

Aspects of the disclosure relate to high-precision measurement of surface stress in chemically strengthened glasses in which the strengthening process (e.g., ion exchange) has induced a decrease in the surface refractive index.

The disclosure comprises the use of prism coupling light with the appropriate wavelength (e.g., infrared) at which the total attenuation in the measured sample due to scattering and absorption is several tens of dB per mm or smaller. While such levels of attenuation are substantial, using prism coupling in combination with image processing can yield precise measurements of surface birefringence and compressive stress where conventional systems cannot make an acceptable measurement. In the case of the glass-ceramics, the attenuation at wavelengths where useful measurements are possible has generally been substantially larger than 1 dB/cm, and in most cases larger than about 1 dB/mm.

The systems and methods disclosed herein are generally applicable to glass-ceramics wherein the ion-exchange process leads to a decrease in the surface refractive index so that the TE and TM spectra contain only radiation (non-guided) modes. The systems and methods are also applicable to some cases wherein the ion-exchange process changes the surface refractive index primarily due to stress through the stress-optic coefficient, but wherein the index change due to a change in the polarizability of the medium is very small and does not lead to formation of an optical waveguide. The systems and methods are also applicable to some cases wherein the ion-exchange process leads to an increase in the surface refractive index, but wherein individual modes are not resolvable in the angular coupling spectrum due to excessive optical attenuation of the sample.

Example systems include at least one light-scattering element in the optical path between the light source and the coupling-prism coupling surface. Example light-scattering elements may include, for example, a rough surface on the coupling-prism input surface or a diffusing film on the coupling-prism input surface. Example light-scattering elements may also include a stand-alone light-scattering element (diffuser) in the optical path between the coupling-prism input surface and the light source. The stand-alone diffuser may be movable to reduce speckle. The at least one light-scattering element can provide a more uniform angular distribution of illumination. In addition, there may be two diffusers in the path between the prism and the light source: a static diffuser optimized for improving the uniformity of angular distribution, and a moving diffuser optimized for reducing speckle in the images of the angular coupling spectra. Various combinations of light-scattering elements may thus be employed.

Other aspects of the disclosure include a system for measuring birefringence. The system includes a controller configured to perform image processing (i.e., signal processing) of the measured TE and TM spectra to measure the stress-induced birefringence. The system is configured to have an angular uniformity of illumination sufficient to achieve a measurement of the birefringence to within 0.00006 refractive-index units (RIU). While the raw measured TE and TM spectra have different shapes by virtue of the different optical effects that occur for different polarizations, the controller is configured (i.e., includes instructions in the form of software embodied in a computer-readable medium) to process these spectra in a manner that minimizes the differences in their shapes. The processed TE and TM spectra are compared in a way that allows for a precise measurement of the shift between their corresponding curves. The shift is measured in pixel widths, which represents width an index resolution or birefringence per pixel of shift. The pixel shift times the index resolution provides a measurement of the birefringence. The birefringence can then be used to calculate surface stress by multiplying by the SOC.

An aspect of the disclosure is a method of optically measuring an amount of birefringence B in a surface of a sample. The sample may be an ion-exchanged glass or glass-ceramic. The method includes: a) digitally capturing TE and TM angular spectra of intensity versus pixel number for the sample, wherein the digital capturing is defined by pixels having an index resolution; b) processing the TE and TM angular spectra to minimize differences between respective regions of the TE and TM angular spectra, wherein the respective regions include a rate of change of intensity with angle that is at least 40% of a maximum rate of change of intensity with angle; c) determining an amount of shift in pixels that best overlaps the processed TE and TM spectra; and d) determining the amount of birefringence B by multiplying the pixel shift by the index resolution.

Another aspect of the disclosure is a method of optically measuring an amount of birefringence B in a surface of a sample made of ion-exchanged glass or a ceramic. The method includes: a) digitally capturing TE and TM angular spectra of intensity versus pixel number for the sample, wherein the digital capturing is defined by pixels having an index resolution; b) optionally normalizing the TE and TM angular spectra to a total-reflectivity spectrum obtained without sample, representative of the angular distribution of the illumination system; c) processing the optionally normalized TE and TM angular spectra to obtain filtered TE and TM spectra; d) calculating respective derivatives of the filtered TE and TM spectra; e) determining the angular locations of respective maxima of the respective derivatives; and determining the shift by the angular separation of the respective derivative maxima.

Another aspect of the disclosure is a system for optically measuring an amount of birefringence B in a surface of a sample made of ion-exchanged glass or a ceramic. The system includes a prism optically coupled to the sample surface at a coupling surface and having an input surface and an output surface. The system has a light source that emits light having an operating wavelength in the infrared range, with the light source optically coupled to the prism coupling surface via the input surface and over a first optical path. The system also includes a photodetector system optically coupled to the prism coupling surface via the output surface over a second optical path and configured to receive TE and TM light representative of TE and TM angular spectra of the sample, wherein the photodetector system includes one or more pixels having an index resolution. The system also has a controller. The controller is electrically connected to the photodetector system and is arranged to receive the TE and TM images. The controller is configured with instructions embodied in a computer-readable medium to process the TE and TM images to minimize differences between respective regions of the TE and TM angular spectra. The respective regions include a rate of change of intensity with angle that is at least 40% of a maximum rate of change of intensity with angle. The controller is configured to determine an amount of pixel shift that best overlaps the processed TE and TM spectra in the respective regions and determine the amount of birefringence B by multiplying the pixel shift by the index resolution.

Additional features and advantages will be set forth in the Detailed Description that follows and in part will be readily apparent to those skilled in the art from the description or recognized by practicing the embodiments as described in the written description and claims thereof, as well as the appended drawings. It is to be understood that both the foregoing general description and the following Detailed Description are merely exemplary and are intended to provide an overview or framework for understanding the nature and character of the claims.

BRIEF DESCRIPTION OF THE DRAWINGS

The accompanying drawings are included to provide a further understanding, and are incorporated into and constitute a part of this specification. The drawings illustrate one or more embodiment(s) and together with the Detailed Description serve to explain the principles and operation of the various embodiments. As such, the disclosure will become more fully understood from the following Detailed Description, taken in conjunction with the accompanying Figures, in which.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

The entire disclosure of any publication or patent document mentioned herein is incorporated by reference.

Cartesian coordinates are shown in some of the Figures for the sake of reference and are not intended to be limiting as to direction or orientation.

Figures 1, 2:
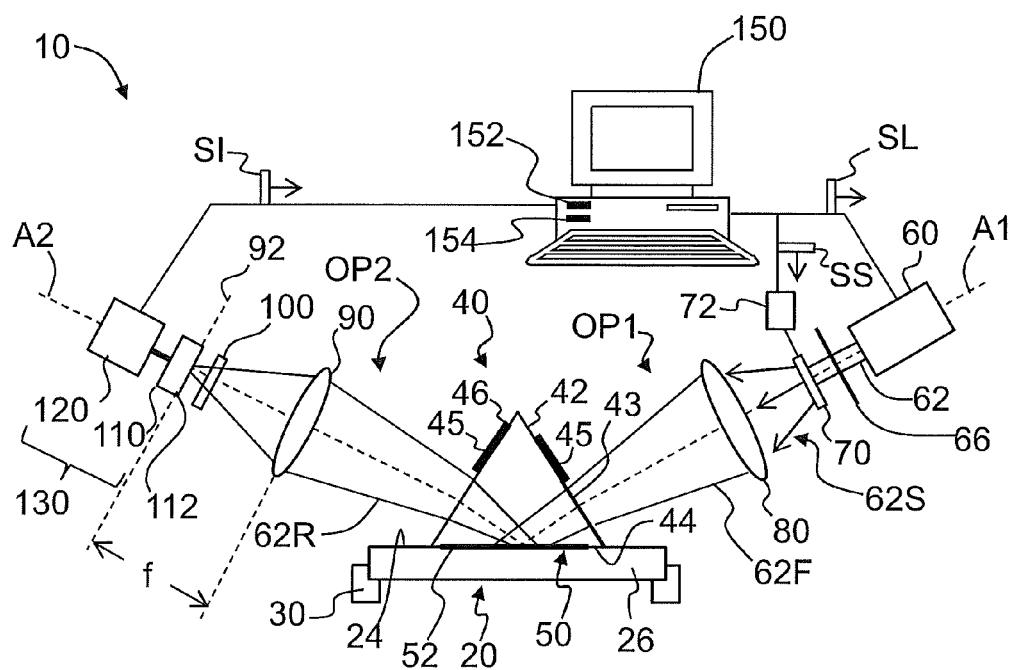
FIG. 1 is a schematic diagram of an example embodiment of a surface-stress measurement system according to the disclosure.
FIG. 2 is an elevated view of the example photodetector system of the surface-stress measurement system of FIG. 1 showing an IR analog detector and a TE/TM polarizer.

FIG. 1 is a schematic diagram of an example near-surface birefringence/stress measurement system ("system") 10 according to the disclosure for measuring an amount of near-surface birefringence/stress in a sample 20. The sample 20 has a top surface 24 and a body or bulk portion 26 with a refractive index $n_s$. In one embodiment, system 10 includes a sample holder 30 configured to hold sample 20. In alternative embodiments, however, sample holder 30 is not required. In one embodiment, sample 20 is held by surface tension of an index-matching liquid that resides between the sample and the prism (introduced and discussed below). In another embodiment, system 10 is inverted so that sample 20 is disposed on the prism coupling surface and is held there by gravity.

In an example, sample 20 has undergone an ion-exchange process whereby ions have been exchanged through top surface 24, thereby changing the refractive index of the sample at (and near) the top surface to a refractive index $n_0$, which may be different for s-polarized light (transverse electric, TE) than for p-polarized light (transverse magnetic, TM), which is polarized parallel to its plane of incidence. This process gives rise to birefringence at and near top surface 24 of sample 20. This birefringence is measured by system 10, and the resulting measurement can be used to calculate the stress at (and near) top surface 24. Measurements of stress and birefringence can be used for process and quality control in the manufacture of ion-exchanged samples 20. Such samples can include chemically strengthened glass and glass-ceramics, similar to GORILLA® glass, made by Corning, Inc., of Corning, N.Y. Sample 20 may be in the form of a substrate, so that in the discussion below sample 20 is also referred to as substrate 20.

The system 10 also includes a coupling prism 40 having an input surface 42, a coupling surface 44 and an output surface 46. The coupling prism 40 has a refractive index $n_p > n_s$. The coupling prism 40 is interfaced with sample 20 by bringing coupling-prism coupling surface 44 and sample top surface 24 into optical contact and thereby defining a sample-coupling prism interface ("interface") 50.

In an example, coupling prism input surface 42 includes a light-scattering portion 43, whose purpose is discussed below. The light-scattering portion 43 may be formed directly on coupling prism input surface 42, such as by roughening the coupling prism input surface. Alternatively, light-scattering portion 43 may be a scattering (e.g., light-diffusing) film or element affixed to coupling prism input surface 42 or may be a separate scattering optical element located between input surface 42 and light source 60.

In an example, light-blocking members 45 are included on one or both of input surface 42 and output surface 46 to eliminate adverse effects from stray light and thereby improve the signal-to-background ratio (SBR).

In an example embodiment, coupling prism 40 has a trapezoidal, curved or other cross-sectional shape instead of the triangular cross-sectional shape that is shown in FIG. 1 by way of illustration. One or more light-blocking element 45 may be positioned on the trapezoidal or other cross-sectional-shaped coupling prism, including on one or more surfaces that are not the input, output, or coupling surface.

In an example, a thin layer of index-matching fluid 52 can be used to facilitate optical coupling between coupling prism 40 and sample 20. The index-matching fluid 52 has a refractive index $n_f$ such that $n_f \geq n_s$, and most often such that $n_p \geq n_f \geq n_s$. In an example, to optimize the measurement accuracy of the surface-stress measurement, refractive index $n_f$ of index-matching fluid 52 is the same or very close to coupling-prism refractive index $n_p$. In examples, the index-matching-fluid refractive index $n_f$ differs from the coupling-prism refractive index $n_p$ by less than about 0.03 or by less than 0.01.

Using a small index difference between index-matching fluid 52 and coupling prism 40 helps reduce the contrast of parasitic fringes that may appear in the partially reflected spectrum (outside the region of total internal reflection) due to coupling resonances with leaky modes of a quasi-waveguide formed between the coupling prism and sample 20. An example coupling-prism refractive index $n_p$ is about 1.6 at an operating wavelength $\lambda$ of 1,550 nm. As discussed below, the coupling-prism refractive index $n_p$ can be selected to optimize the performance of system 10 based on the characteristics of sample 20.

With continuing reference to FIG. 1, system 10 includes optical axes A1 and A2 that respectively pass through input and output surfaces 42 and 46 of coupling prism 40 to generally converge at coupling prism interface 50 after accounting for refraction at the prism/air interfaces. The system 10 includes, in order along axis A1, a light source 60 that emits light 62, an optional optical filter 66 that may be alternatively included in the detector path on axis A2, an optional light-scattering element 70, and an optional focusing optical system 80 that forms focused light 62F as explained below. Thus, in an example of system 10, there are no optical elements between light source 60 and prism input surface 42.

The system 10 also includes, in order along axis A2 from coupling prism 40, a collecting optical system 90 having a focal plane 92 and a focal length f and that receives reflected light 62R as explained below, a TM/TE polarizer 100, and a photodetector system 130. The axis A1 defines the center of an optical path OP1 between light source 60 and coupling-prism coupling surface 44. The axis A2 defines the center of an optical path OP2 between coupling surface 44 and photodetector system 130. Note that axes A1 and A2 may be bent at input and output surfaces 42 and 46, respectively, due to refraction.

In an example, photodetector system 130 includes an IR analog detector (camera) 110 and a frame grabber 120. In other embodiments discussed below, photodetector system 130 includes a CMOS or CCD camera, single-element photodiodes, or one or two linear photodetectors (i.e., a line of integrated photodiodes or photo-sensing elements). The photodetector system may also employ one or more microbolometers, a microbolometer camera, one or more InGaAs-based photodetectors, or an InGaAs camera. The photodetector system 130 includes a photosensitive surface 112, which is shown by way of example as the photosensitive surface of IR analog detector 110. The photosensitive surface 112 resides in focal plane 92 of collecting optical system 90, with the photosensitive surface being generally perpendicular to axis A2. This serves to convert the angular distribution of light 62R exiting the coupling prism to a transverse spatial distribution of light at the sensor plane of camera 110.

In an alternative embodiment in which the focal length f is larger than 5 times the size of the photosensitive surface 112, this surface may be tilted with respect to the axis A2 for a moderate increase in the sensitivity of position along x to the effective index. The photodetector system 130 generates an image signal SI, as described below. In the example system of FIG. 1, image signal SI is shown as being generated by frame grabber 120. The frame grabber 120 serves to digitize the analog image from IR analog detector 110 in order to define pixels that have an associated refractive index equivalent. The refractive index equivalent of one pixel can be deemed a refractive index resolution $\delta n_{pix}$, as dictated by the pixel resolution of photodetector system 130.

In an example, the pixel resolution (i.e., the spacing between two neighboring pixels) equals approximately the product of the refractive index resolution, the focal length f of collecting optical system 90, and the sensitivity of the exit angle of light rays in optical path OP2 to change in the effective index under measurement.

Example light sources 60 include infrared lasers, infrared light-emitting diodes, infrared amplified-spontaneous-emission (ASE) sources, infrared super-luminescent-diode (SLD) sources, and broader-bandwidth sources such as hot-filament lamps and quartz lamps combined with proper means of narrowing the optical spectrum including wavelength-selective filters or diffraction gratings. Example operating wavelengths λ of light 62 generated by light source 60 include infrared wavelengths, such as (nominally) 940 nm, 1,060 nm, 1,550 nm, 1,613 nm, 1,900 nm or 2,200 nm.

It has been recognized that a range of glass-ceramics of commercial interest could be measured with adequate precision with a system operating in the infrared range of wavelengths. In one example, the operating wavelength λ is longer than about 1,400 nm. In another example, the operating wavelength λ is longer than about 1,500 nm. In yet another example, the operating wavelength λ is longer than about 1,800 nm. In an alternative example, the operating wavelength is longer than about 820 nm, and depending on the attenuation properties of the measured samples such as absorption and scattering it may need to be longer than about 900 nm or 1000 nm. These near-infrared wavelength ranges are well suited for detection using CMOS or CCD cameras, in which case the wavelength is also desirably shorter than about 1100 nm.

On the other hand, in one example, the operating wavelength λ is shorter than about 7,500 nm, and, in another example, the operating wavelength λ is shorter than about 5,500 nm.

Three exemplary operating wavelength regions are 1,530 nm≤λ≤1,650 nm, 1,900 nm≤λ≤2,800 nm, and 2,900 nm≤λ≤4,700 nm. Another example region is 3,300 nm≤λ≤4,600 nm, which in a more specific example is 3,400 nm≤λ≤4,500 nm.

When the operating wavelength λ is longer than about 2,200 nm, some of the optical elements in system 10, such as coupling prism 40, focusing optical system 80, collecting optical system 90, filter 66, light-scattering element(s) 70, and TE/TM polarizers 100, may need to be made of materials that are substantially transparent at the operating wavelength. Such materials with a high enough index to serve as coupling prism 40 include ZnSe, ZnTe, Yttrium Aluminum Garnet (YAG), Si, LiTaO₃ and sapphire, among others.

When birefringent materials such as sapphire are used, a calibration needs to be performed, since a shift of the total-internal-reflection (TIR) transition between the TE and the TM region may be observed due to the birefringent materials even when measured substrate 20 has no surface birefringence. Appropriate materials for the lenses, filters, and diffusers of system 10 include CaF₂, MgF₂, ZnSe, Si, various oxide crystals and some thin plastics, which are especially useful when shaped as Fresnel lenses.

In an example, the operating wavelength λ is approximately equal to or longer than the average diameter of the micro- or nano-crystals that make up sample 20. For example, an operating wavelength of λ=1,550 nm may be used for measuring the stress-induced birefringence of a white glass-ceramic sample 20 wherein the largest crystals have a dimension of about 800 nm. In another example, the operating wavelength λ may be selected to be at least five times larger than the typical size of micro- or nano-crystals whose refractive index is significantly higher than that of the glass matrix of the measured glass-ceramic sample. Alternatively, in some cases the operating wavelength λ may be selected to be substantially larger than the average spacing of such high-index micro crystals.

An ASE-based light source 60 may be fiber-based, as in the case of, for example, a diode-pumped erbium-doped fiber amplifier (EDFA), or may comprise a super-luminescent diode (SLD) instead of a diode-pumped EDFA. This can help reduce the cost of light source 60, as well as make it more compact, and can in some cases help increase bandwidth in order to reduce speckle.

An ASE-based light source 60 that operates near λ=1,550 nm can be replaced by an LED-based light source when an adequate signal-to-noise ratio (SNR) can be obtained by using an IR analog detector 110 of suitable sensitivity.

A laser-based light source 60 can be advantageous because it can have high power and brightness, e.g., optical power within a desired angular and spectral range. Since optical attenuation in the operating wavelength range of 1,400 nm≤λ≤1,500 nm in samples 20 may be only slightly higher than it is in the range 1,530 nm≤λ≤1,570 nm, commercially available diode lasers normally used as pump lasers for EDFAs, with wavelengths in the range 1,400 nm to 1,500 nm, may be employed in certain cases. To increase the bandwidth in order to reduce speckle, the pump laser can be wavelength-modulated by modulating the laser current. In addition, multiple pump lasers can be used. In examples, one or more of laser current modulation, multiple lasers, and a moveable light-scattering element 70 can be employed to reduce speckle to an acceptable level.

Thus, in one example, light-scattering element 70 is movable such that the adverse effects of speckle due to the coherence of light 62 are reduced. For example, light-scattering element 70 can be in the form of a rotating and light-diffusing disk. The speckle reduction can be accomplished by producing multiple uncorrelated speckle patterns that are then time-averaged to reduce speckle-induced image noise. In an example, light-scattering element 70 is a diffuser. The light-scattering element 70 can be used as the only light-scattering member, in combination with light-scattering portion 43 of coupling prism input surface 42, or in combination with a stand-alone static scattering member disposed in optical path OP1.

Likewise, light-scattering portion 43 can be employed as the only light-scattering member in system 10. The combination of two or more light-scattering elements 70 can provide a substantial breadth to and improve the uniformity of the angular spectrum that illuminates interface 50. In an example, light-scattering element 70 is operably connected to a drive unit 72 that controls the movement (e.g., rotation, vibration, etc.) of the light-scattering element in response to a control signal SS. In an example, a controller 150 may be operably connected to drive unit 72 to control the operation of the drive unit via control signal SS in order to effectuate the movement of light-scattering element 70. In another example, drive unit 72 is not connected to controller 150 and is manually activated and de-activated, or may be activated and de-activated by a switch that is operating synchronously with the power switch of light source 60.

The focusing optical system 80 may be used to generally adjust the angular spectral content interacting with sample 20 through interface 50. However, in some embodiments of system 10, focusing optical system 80 is not required. For example, the use of one or more light-scattering elements 70 (e.g., light-scattering surfaces) can create a sufficiently broad and adequately uniform angular distribution at coupling surface 44 of coupling prism 40.

Either focusing optical system 80 or collecting optical system 90, or both, can include a curved reflective surface, or can each comprise multiple optical elements, including refractive and/or reflective elements. The focusing optical system 80 may include as one of its surfaces a light-scattering surface to provide a broader or more uniform angular distribution of light 62 directed to interface 50, and to provide a more uniform light distribution downstream of the focusing optical system.

FIG. 2 is a close-up elevated view of IR analog detector 110 and TE/TM polarizer 100. The TE/TM polarizer 100 includes adjacent sections 100TE and 100TM that have TE and TM polarizing elements, respectively. The sections 100TE and 100TM respectively define corresponding TE and TM sections 112TE and 112TM on photosensitive surface 112. TE/TM polarizer 100 may have more than one TE section 100TE or more than one TM section 100TM. In an example, TE/TM polarizer 100 includes three or more total polarizer sections 100TM and 100TE. In one embodiment, polarizer sections 100TE and 100TM may be spatially alternating between TE and TM sections 100TE and 100TM such that no TE sections are adjacent to TE sections, or no TM sections are adjacent to TM sections. In another embodiment, TE and TM polarizer sections 100TE and 100TM may be arranged such that some TE sections are adjacent to other TE sections, or some TM sections are adjacent to other TM sections.

In other embodiments, TE/TM polarizer 100 may comprise a single polarizing element that is sequentially rotated between two approximately orthogonal states for obtaining the TE and TM spectra. In other embodiments discussed below, two separate photosensitive surfaces 112 associated with separate IR analog detectors 110 are employed.

The system 10 includes controller 150, which is configured to control the operation of the system. The controller 150 is also configured to receive and process image signals SI from photodetector system 130 that are representative of (raw) TE and TM spectra, as described below. The controller 150 includes a processor 152 and a memory unit ("memory") 154. The controller 150 may control the activation and operation of light source 60 via a light-source control signal SL, and receives and processes image signals SI from photodetector system 130 (e.g., from frame grabber 120, as shown).

In an example, controller 150 comprises a computer and includes a reading device, for example, a floppy disk drive, a CD-ROM drive, a DVD drive, a magnetic optical disk (MOD) device (not shown), or any other digital device including a network-connecting device, such as an Ethernet device (not shown), for reading instructions and/or data from a computer-readable medium, such as a floppy disk, a CD-ROM, a DVD, a MOD, a flash drive, or another digital source such as a network or the Internet. The controller 150 is configured to execute instructions stored in firmware and/or software (not shown), including signal-processing instructions for carrying out the surface birefringence/stress measurements disclosed herein. In examples, the terms "controller" and "computer" are interchangeable.

The controller 150 is programmable to perform the functions described herein, including the operation of system 10 and the aforementioned signal processing of image signals SI in order to arrive at a measure of the surface birefringence/stress. As used herein, the term "computer" is not limited to just those integrated circuits referred to in the art as computers, but broadly refers to computers, processors, microcontrollers, microcomputers, programmable logic controllers, application-specific integrated circuits, and other programmable circuits, and these terms are used interchangeably herein.

Software may implement or aid in the performance of the operations of system 10 disclosed herein, including the aforementioned signal processing. The software may be operably installed in controller 150 and in particular in processor 152 and memory 154. Software functionalities may involve programming, including executable code, and such functionalities may be used to implement the methods disclosed herein. Such software code is executable by the general-purpose computer or by the processor unit described below.

In operation, the code and possibly the associated data records are stored within a general-purpose computer platform, within processor 152 and/or in memory 154. At other times, however, the software may be stored at other locations and/or transported for loading into the appropriate general-purpose computer systems. Hence, the embodiments discussed herein involve one or more software products in the form of one or more modules of code carried by at least one machine-readable medium. Execution of such code by processor 152 of computer system 150 or by the processor unit enables the platform to implement the catalog and/or software downloading functions in essentially the manner performed in the embodiments discussed and illustrated herein.

The computer 150 and/or processor 152 may each employ a computer-readable medium or machine-readable medium (e.g., memory 154), which refers to any medium that participates in providing instructions to the processor for execution, including, for example, determining an amount of surface birefringence/stress in sample 20. The memory 154 constitutes a computer-readable medium. Such a medium may take many forms, including but not limited to non-volatile media, volatile media and transmission media. Non-volatile media include, for example, optical or magnetic disks, such as any of the storage devices in any computer(s) operating as one of the server platforms discussed above. Volatile media include dynamic memory, such as the main memory of such a computer platform. Physical transmission media include coaxial cables, copper wire and fiber optics, including the wires that comprise a bus within a computer system.

Common forms of computer-readable media therefore include, for example, a floppy disk, a flexible disk, a hard disk, magnetic tape, flash drives and any other magnetic medium; a CD-ROM, a DVD and any other optical medium; less commonly used media such as punch cards, paper tape and any other physical medium with patterns of holes; a RAM, a PROM, an EPROM, a FLASH-EPROM and any other memory chip or cartridge; a carrier wave transporting data or instructions, cables or links transporting such a carrier wave, or any other medium from which a computer can read programming code and/or data. Many of these forms of computer-readable media may be involved in carrying one or more sequences of one or more instructions to processor 152 for execution.

In the general operation of system 10, controller 150 may send control signal SL to light source 60 in order to activate and control the operation of the light source. Alternatively, light source 60 can be manually activated. The light source 60 emits light 62, which travels toward coupling surface 44 along axis A1. This light 62 passes through optical filter 66, if present. The optical filter 66 may be disposed in either of optical paths OP1 and OP2. The light 62 may then be scattered by light-scattering element 70 to form scattered light 62S. The scattered light 62S may be received by focusing optical system 80, which generally redirects the scattered light. The term "focused light" 62F refers to this generally redirected light formed with or without scattering element 70, and characterized with an angular spectrum or range of incidence angles. The focused light 62F passes through coupling prism input surface 42, which may include light-scattering portion 43. The focused light 62F is incident upon interface 50 over an angular range. The focused light 62F is reflected at interface 50 to form reflected light 62R, which travels to collecting optical system 90.

Because of the nature of interface 50, reflected light 62R includes information about sample top surface 24 via the interaction of the evanescent field with sample 20. The reflected light 62R exits coupling prism output surface 46 and travels to collecting optical system 90, which collects the reflected light and directs it through TE/TM polarizer 100 and forms an image on photosensitive surface 112 of photodetector system 130.

The image formed on photosensitive surface 112 is a representation of the angular spectrum of reflection off of interface 50. This reflection of light at interface 50 involves the interaction of focused or angularly dispersed light 62F with underlying sample surface 24 due to the aforementioned evanescent field associated with the total internal reflection from the interface. This interaction involves an effective shift between the location at which focused light 62F is incident upon interface 50 and the location from which reflected light 62R leaves the interface. This shift is known as the Goos-Hänchen shift, and the length of this shift may be used as an approximate estimate of an interaction length of light 62 with sample surface 24. An aspect of the method of operation of system 10 includes selecting this interaction length by the choice of the refractive index of coupling prism 40 to account for the optical attenuation of sample 20 at the measurement wavelength. In an example, the prism refractive index $n_p$ at the operating wavelength is between 1.54 and 1.8. In another example, $n_p$ is between 1.8 and 4.

In an example, IR analog detector 110 detects the image formed by collecting optical system 90 and generates an analog image signal (not shown) that is sent to frame grabber 120. The frame grabber 120 digitizes the analog image signal to form digital image signal SI. The configuration of TE/TM polarizer 100 allows for both TE and TM light to form images on corresponding sections of photosensitive surface 112. Thus, the image formed by collecting optical system 90 using the example TE/TM polarizer 100 shown in FIG. 2 includes both TE section 100TE and TM section 100TM, which are adjacent one another. The image signal SI from photodetector system 130 thus includes image information from each of these sections. The TE and TM information provided by TE and TM sections 112TE and 112TM of photodetector surface 112 represents the TE and TM spectra, which can be used to determine the amount of birefringence in surface 24 of sample 20. As discussed above, TE/TM polarizer can include more than one TE section 100TE and more than one TM section 100TM so that in other embodiments there can be more than one TE section 112TE and more than one TM section 112TM.

While for wavelengths in the range 1,100 nm to 2,400 nm IR analog detector 110 and frame grabber 120 can be replaced by a higher-resolution digital photodetector such as an InGaAs camera, the configuration of photodetector system 130 as shown and described in FIG. 1 is advantageous from a cost viewpoint. The IR analog detector 110 may also comprise, for example, a PbSe detector or camera that operates in the wavelength range of 800 nm to 5,000 nm; a HgCdTe detector or camera that operates in the wavelength range between 2,000 nm and about 10,000 nm; a PbS, an InAs, an InSb, or like detectors that operate in the wavelength range from about 2,000 nm to about 10,000 nm, more specifically, between about 3,000 nm and about 5,000 nm. The IR analog detector 110 may be a line-scan camera or one or more 1×N detectors, or one or more (a few lines)×N, where N is the number of pixels per line. An example digital resolution of system 10 is about 20 microns per pixel.

It is counterintuitive that such a low digital image resolution could actually be used to obtain a relatively high-precision measurement (i.e., on the order of $10^{-5}$ RIU) of the surface birefringence in sample 20. However, the signal processing methods disclosed herein make possible the successful use of IR analog detector 110 and frame grabber 120 in achieving such a high-precision measurement.

The IR analog detector 110 has the advantage of being sensitive at significantly longer wavelengths, up to, for example, about 2,200 nm, than are CMOS or CCD sensors. It has been determined that such longer wavelengths, especially wavelengths longer than 1,500 nm, for example, are advantageous for measuring surface birefringence in a majority of glass-ceramics of present commercial interest, and in particular in many white glass-ceramics.

In some applications of system 10, a near-infrared operating wavelength $\lambda$ in the range 800 nm $\leq \lambda \leq$ 1,100 nm may be employed. In such cases, a CMOS or CCD sensor can be used to form photodetector system 130.

Figure 3A:
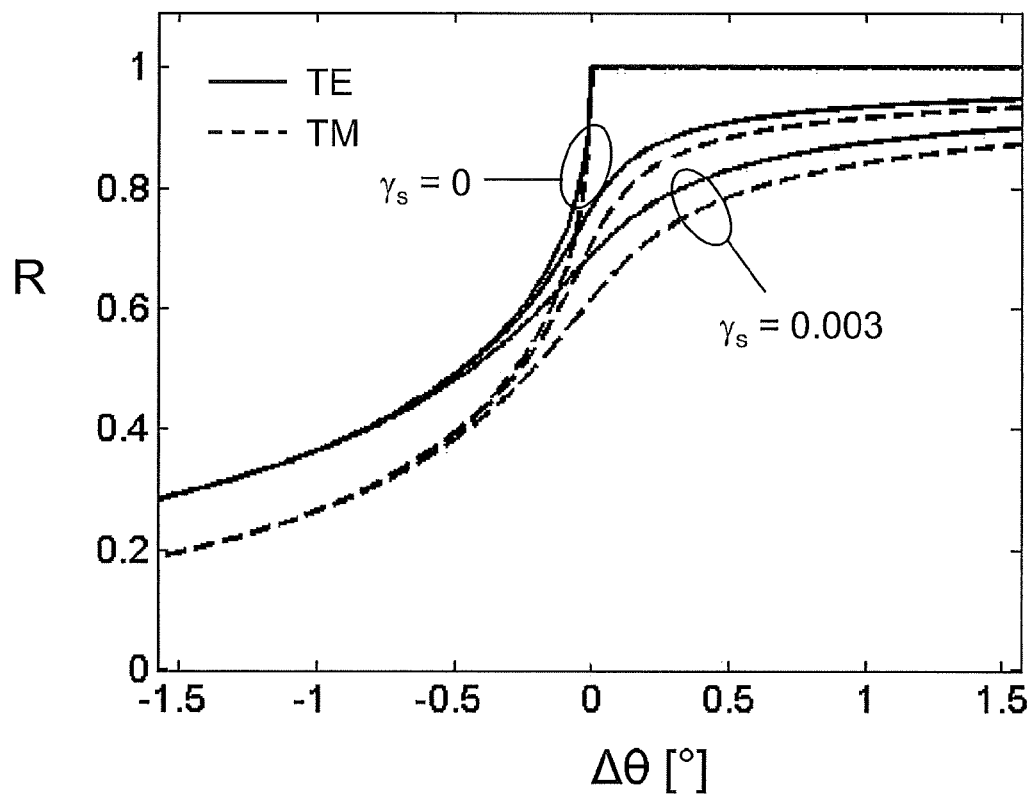
FIG. 3A plots reflectivity R versus $\Delta\theta=\theta-\theta_C$ (in degrees) for TE light (solid line) and TM light (dashed line)

There is an angle $\theta_C$ called the critical angle at which the internal reflection of focused light 62F from interface 50 becomes total internal reflection (TIR). The TE and TM polarizations of light 62 will have different critical angles $\theta_C$, which are denoted herein as $\theta_{C\text{-}TE}$ and $\theta_{C\text{-}TM}$. FIG. 3A plots reflectivity R versus $\Delta\theta=\theta-\theta_C$ (in degrees), which is the difference between the incidence angle and the critical angle $\theta_C$. FIG. 3A shows calculated TE (solid line) and TM (dashed line) reflectivity in the region around the critical angle $\theta_C$ for a simple, uniform-index substrate 20 for various levels of optical attenuation in the substrate $\alpha_s$ and associated with it normalized attenuation $\gamma_s$ as described below, $\gamma_s$ taking on values 0, 0.0015, and 0.003. The sharp corner occurs for the case of no attenuation, and the transition becomes progressively smoother (and the corner progressively duller) with increasing attenuation.

Figure 3B:
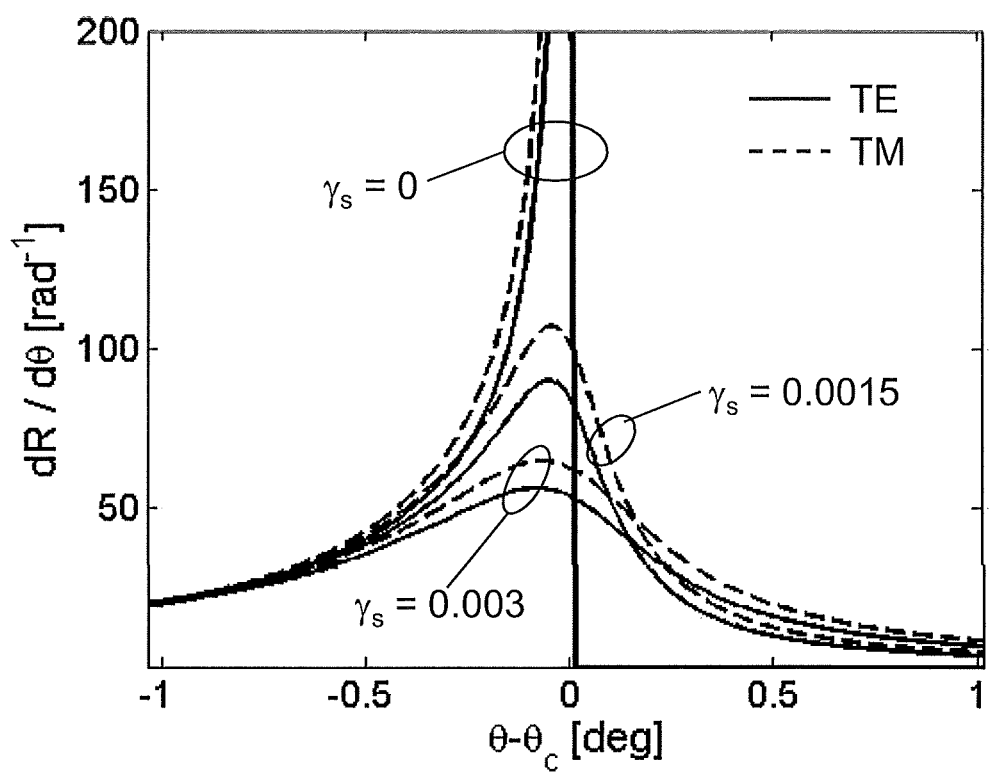
FIG. 3B plots the derivative of reflectivity R with angle $\theta$ versus angle $\theta$ (in degrees) for TE light (solid line) and TM light (dashed line)

FIG. 3B is similar to FIG. 3A and shows the derivative of the function reflectivity R as a function of angle $\theta$ for three levels of normalized attenuation in the substrate $\gamma_s$ equal to 0, 0.0015 and 0.0030, where $\gamma_s=\kappa_s n_p/n_s^2$, and $\kappa_s=\alpha_s\lambda/4\pi$ is the imaginary part of the complex refractive index representing the substrate with attenuation $\alpha_s$. I the particular example of FIG. 3B, $n_p=1.14 n_s$. These values of normalized attenuation $0 \leq \gamma_s \leq 0.003$ encompassing the range from 0 to approximately the highest attenuation levels where accurate measurements of practical importance are possible by using the methods of the present disclosure.

The plots for TE-polarized light are shown as continuous lines, while those for TM-polarized light are shown as dashed lines. The peak of the derivative as a function of angle becomes progressively broader and smaller in magnitude with increasing of $\gamma_s$. The plot of FIG. 3B shows that the peak of the derivative signal stays within 0.1 degree of the critical angle $\theta_C$ of calculated for the lossless-substrate case. In addition, the difference between the peaks of the derivative signal for TE polarization and the derivative signal for TM polarization is much smaller than 0.1 degree and is thus usually negligible.

It is also seen in FIG. 3B that the full-width half-maximum (FWHM) breadth of the derivative signal increases with attenuation, while the maximum derivative decreases. With $n_s=1.535$ and $n_p$ slightly larger than $n_s$ as described above, the value $\gamma_s=0.003$ at the top of the considered range corresponds to $\alpha_s\lambda=0.0162\pi$.

Figure 3C:
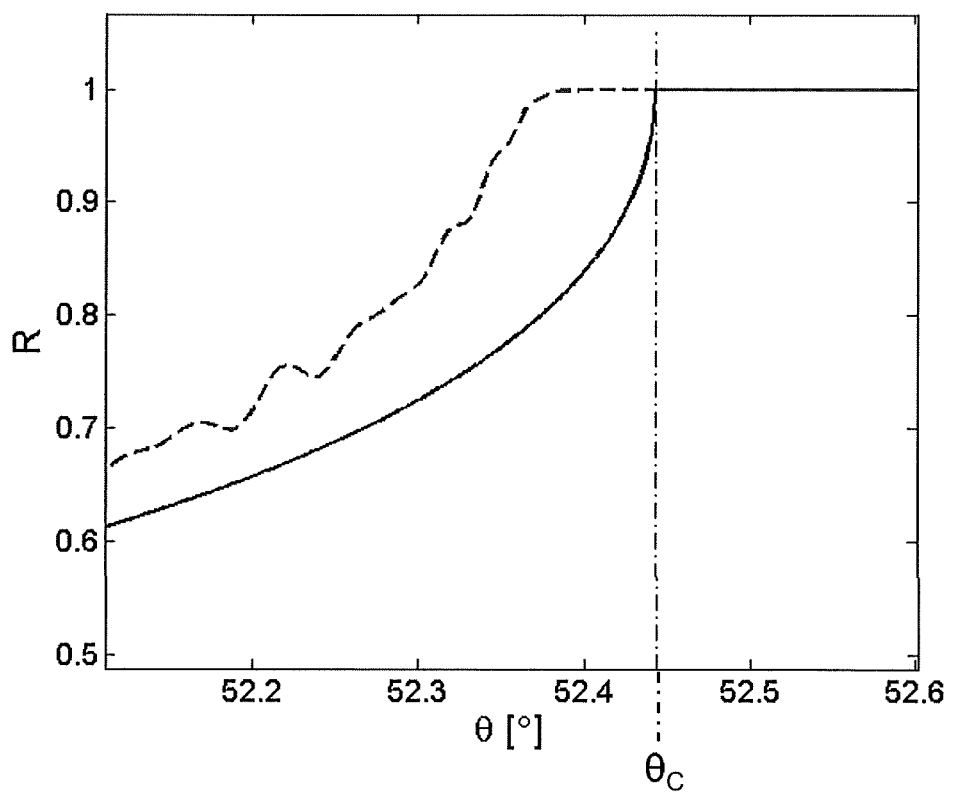
FIG. 3C plots reflectivity R versus $\theta$ (in degrees) for TE light (solid line) and TM light (dashed line) from a numerical simulation of a model ion exchanged glass with decreased refractive index at the surface.

FIG. 3C plots reflectivity R versus angle $\theta$ (degrees) and illustrates the effect of index profile on the shape of the transition region around the critical angle $\theta_C$, which is marked by the vertical dash-dotted line (TE-case only). The solid TE curve transitions to TIR without losses when the index $n_s$ of substrate 20 does not vary with depth into the substrate. The dashed curve shows a shift in the transition and a rounding (dulling) of the edge when the index near the surface 24 of substrate 20 monotonically changes with depth, starting at a value at the surface that is lower than the bulk index by 0.002. The shape of the index profile for sample 20 is given by $n(z)=n_s-(0.002)\cdot\text{erfc}(z/50)$ in this case, with z being the depth in micrometers into substrate 20 and $n_s$ the aforementioned substrate bulk refractive index prior to the near-surface index modification.

The smearing of the transition makes it difficult to precisely measure the location of the edge by looking for a sudden change in derivative. The method disclosed herein includes using filtering of the signal to smooth out the ripples, and then comparing the TE and TM signals in the regions of steepest change, e.g., maximum derivative.

Thus, the transition to TIR is normally abrupt when substrate 20 that is measured has negligible optical attenuation and a homogeneous refractive index. In the presence of strong optical attenuation in measured substrate 20, and especially in the presence of strong scattering, the transition to TIR does not happen abruptly. In many prior art measurement systems, the transition is so gradual that it cannot be accurately detected for certain types of samples 20.

In addition, in some ion-exchanged glasses wherein the ion exchange leads to a decrease in the surface refractive index, the surface index distribution yields a moderate smoothing of the abrupt part of the transition to TIR (e.g., a rounding of the sharp feature in the vicinity of the TIR angle in the angular spectrum). This substantially reduces the precision with which existing measurement methods can measure the critical angle for the two polarizations and, in turn, the associated surface birefringence. The range of incident angles of focused light 62F at interface 50 must be sufficient to measure the location of what is called the edge of total internal reflection (ETIR) for each of the angular TE and TM spectra, occurring nominally at the critical angle.

It has been observed that in certain opaque glass-ceramic samples 20, the transition from TIR to partial reflection (hereinafter, the TIR/PR transition) occurs over a progressively narrower angular range as the operating wavelength $\lambda$ increases from the visible to the infrared. Thus, an aspect of the disclosure employs the aforementioned infrared operating wavelength to make the TIR/PR transition more pronounced. This in turn leads to a more accurate measurement of the birefringence.

Figure 4A:
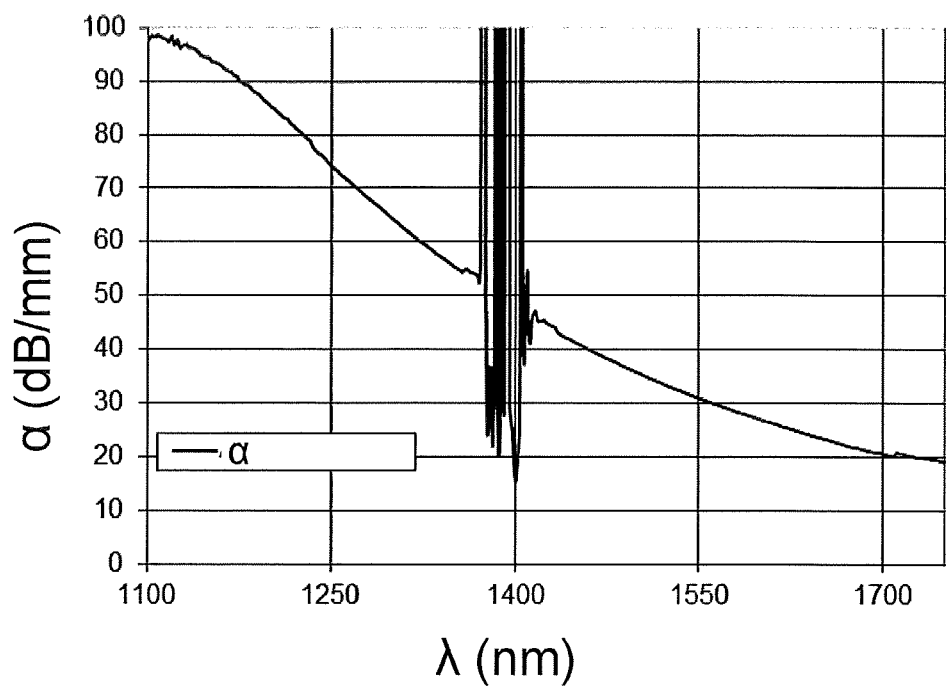
FIGS. 4A and 4B are plots of attenuation $\alpha$ (dB/mm) versus wavelength (nm) for a white glass-ceramic sample having a thickness of 0.351 mm (FIG. 4A) and a black glass-ceramic sample having a thickness of 0.80 mm (FIG. 4B)

FIG. 4A is a plot of substrate attenuation $\alpha_s$ (dB/mm) versus wavelength $\lambda$ (nm) and shows the attenuation of electromagnetic radiation through example sample 20, which consisted of a white glass-ceramic material having a polished top surface 24. The plot covers a wavelength range from 1,100 nm to 1,750 nm. The thickness of example sample 20 was 0.35 mm. The spiked region of the plot at about 1,400 nm is a remnant of the absorption of the optical fiber used to make the attenuation measurement and can be ignored. The plot of FIG. 4A indicates that the attenuation increases significantly with decreasing wavelength, approaching 100 dB/mm at 1,100 nm.

Figure 4B:
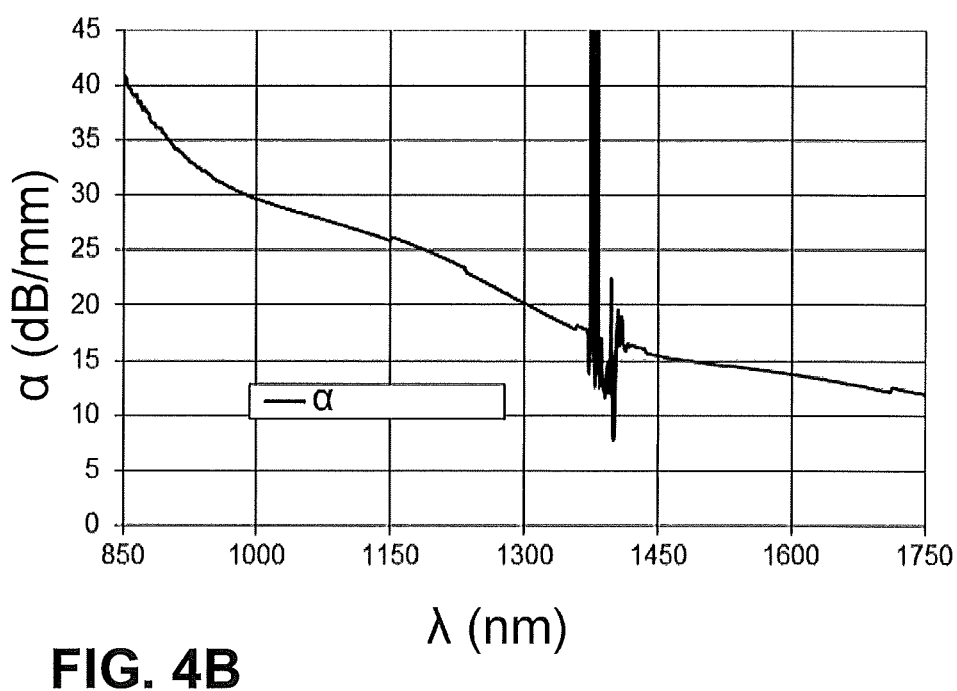

FIG. 4B is a similar plot for an example sample 20 in the form of a black glass-ceramic. The sample thickness was 0.8 mm, and the wavelength range is 850 nm to 1,750 nm. As in FIG. 4A, the spiked portion should be ignored. As with the white glass-ceramic, the attenuation increases significantly with decreasing wavelength. In addition, the attenuation of the black glass-ceramic at wavelengths longer than 1,000 nm is smaller than the attenuation of the white glass-ceramic at 1,550 nm.

The data of FIGS. 4A and 4B indicate that significant attenuation due to scattering and in some cases absorption may be associated with the significantly broader TIR/PR transition. Based on the observed correlation between significant attenuation and the increasing breadth of the TIR/PR transition, along with the lower attenuation observed in black glass-ceramics, it follows that if system 10 can be configured to measure the stress-induced birefringence in white glass-ceramics at a wavelength near 1,550 nm, then it can be configured to measure stress-induced birefringence in black glass-ceramics at a wavelength in the range 1,000 nm to 1,100 nm. This is provided that the stress-optic coefficient of the black glass-ceramic is not significantly smaller than that of the white glass-ceramic.

As described later in the present disclosure, a figure of merit relevant to measurement capability is the product of the wavelength and the attenuation coefficient; hence, a system configured to measure at 1,550 nm and with a certain precision the surface birefringence of the white glass-ceramic of FIG. 4A should be capable of measuring with a similar precision the black glass-ceramic of FIG. 4B at wavelengths at least as short as 850 nm, and possibly as short as 800 nm. Such a system may utilize a CMOS or CCD sensor as the detector, thereby reducing system cost.

Figure 5:
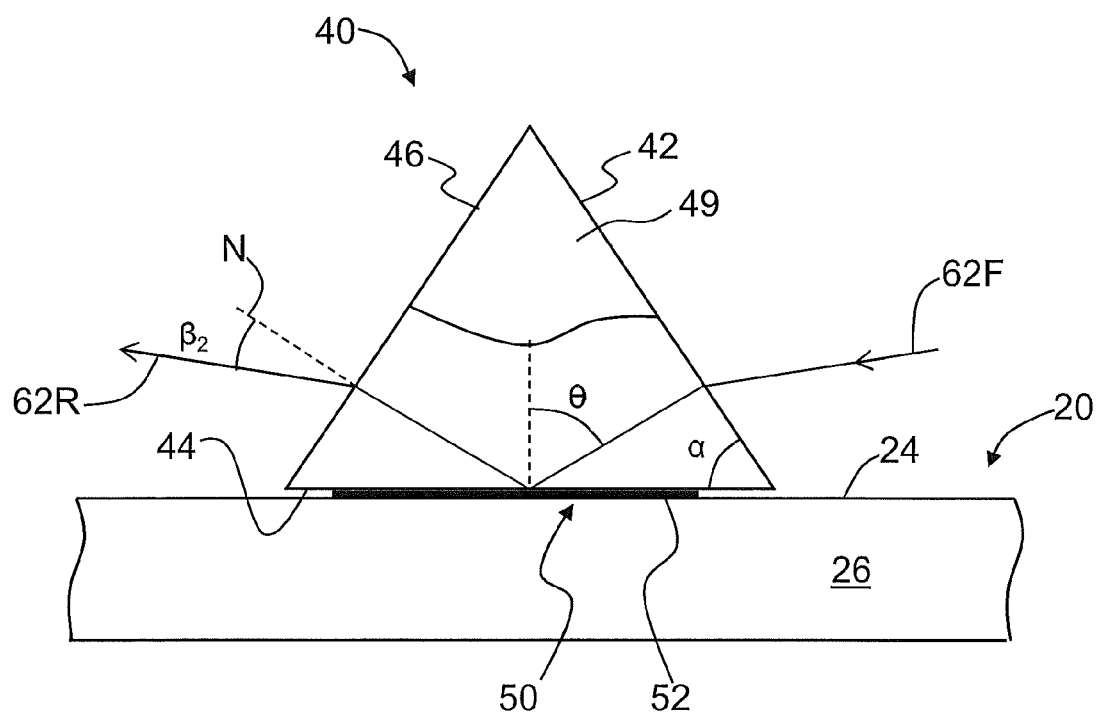
FIG. 5 is a close-up side view of a coupling prism and a sample illustrating the key angles associated with the coupling prism and the focused and reflected light.

FIG. 5 is a close-up view of coupling prism 40 and sample 20 that illustrates the key angles associated with the coupling prism and focused and reflected lights 62F and 62R. In an example, coupling prism 40 is configured as an isosceles triangle in a cross-section. In an example, the isosceles triangle has a corner angle $\alpha=60°$. The focused light 62F incident upon interface 50 at an angle $\theta$ exits coupling prism output surface 46 at angle $\beta_2$ with respect to the surface normal N.

In an example, the optical path between collecting optical system 90 has a focal length f (corresponding to focal plane 92) and photosensitive surface 112 of IR analog detector 110 is located a distance f away from the collecting optical system. In such a configuration, reflected light 62R corresponding to parallel rays (or plane waves) is focused into points on photosensitive surface 112.

Splitting photosensitive surface 112 into TE and TM sections 112TE and 112TM allows for the simultaneous recording of the angular reflection spectra for the TE and TM polarizations of reflected light 62R. This simultaneous detection eliminates a source of measurement noise that could arise from making the TE and TM measurements at different times, given that system parameters can drift with time.

Simultaneously collecting the full angular spectrum of reflection from interface 50 in the vicinity of the ETIR at both TE and TM polarizations is also advantageous for the fast (high-throughput) measurements necessary for quality control and the monitoring of the fabrication of ion-exchanged glasses and glass-ceramics in a commercial setting. Collecting the TE and TM spectra sequentially can also be done relatively quickly using the optical arrangements of the present disclosure, when a single polarizer is sequentially rotated between two mutually orthogonal polarization states. This type of sequential collection of spectra retains the major advantage of avoiding having to move parts over sequential incidence-angle-scanning collections of spectra. This advantage helps to substantially reduce random error in the measured birefringence due to motor lag or to imperfect referencing at each scan.

For the measurement configuration of system 10 of FIG. 1, a plane wave of light 62 propagating in coupling prism 40 with refractive index $n_p$ at angle $\theta$ with respect to the interface normal as shown in FIG. 5 can be phase-matched to a guided, quasi-guided, or radiation propagation mode of sample 20 with an effective refractive index $n_{eff}$ when the following relationship holds:

$$n_{eff} = n_p \sin\theta \quad (1)$$

When the input and output surfaces 42 and 46 have equal dimensions in the plane of the drawing of FIG. 1, the exit angle $\beta_2$ with respect to the surface normal N the coupling prism output surface that corresponds to the effective index $n_{eff}$ is given by $$\beta_2 = \cos^{-1}\sqrt{1 + \sin 2\alpha n_{eff}\sqrt{n_p^2 - n_{eff}^2} - n_{eff}^2 \cos^2\alpha - (n_p^2 - n_{eff}^2)\sin^2\alpha} \quad (2)$$

The sensitivity of the exit angle $\beta_2$ to changes in the effective index $n_{eff}$ is given by:

$$\frac{d\beta_2}{dn_{eff}} = \frac{\cos\alpha + \frac{n_{eff}}{\sqrt{n_p^2 - n_{eff}^2}}\sin\alpha}{\sqrt{1 + \sin 2\alpha n_{eff}\sqrt{n_p^2 - n_{eff}^2} - n_{eff}^2 \cos^2\alpha - (n_p^2 - n_{eff}^2)\sin^2\alpha}} \quad (3)$$

In an example, for sample 20 with a refractive index $n_s=1.536$ and coupling prism 40 with a refractive index $n_p=1.5948$ and angle $\alpha=\pi/3$ radians, $d\beta_2/dn_{eff}=3.85$ radians/RIU, or 0.0022 deg. per $10^{-5}$ RIU, where RIU stands for "refractive index units," with $10^{-5}$ RIU=0.00001). In this example, a change of $10^{-5}$ RIU in the effective index $n_{eff}$ corresponds to $3.85 \times 10^{-5}$ rad change in exit angle.

When photosensitive surface 112 of IR analog detector 110 is approximately perpendicular to axis A2, the spacing $\Delta x$ of two lines formed on the photosensitive surface and representing different prism-coupling angles relates to the effective index separation $\Delta n_{eff}$ of their corresponding phase-matched sample propagation modes through the simplified expression:

$$\Delta x \approx f\Delta\beta_2 = f\frac{d\beta_2}{dn_{eff}}\Delta n_{eff} \quad (4)$$

where f is the aforementioned focal length of collecting optical system 90, and x is the x-direction of photosensitive surface 112, as shown in FIG. 2.

Equation (4) can be used in reverse to determine the typical refractive index resolution of the optical system comprising coupling prism 40 and IR analog detector 110. If the resolution of photodetector system 130 is $\delta x$ (i.e., a pixel size of $\delta x$), then the typical resolution of the effective index measurement (and hence of the birefringence measurement) is on the order of:

$$\delta n_{pix} = \frac{\delta x}{f\frac{d\beta_2}{dn_{eff}}} \quad (5)$$

The standard deviation of the measurement of birefringence can be different from the birefringence resolution defined by equation (5). For example, when system 10 has a highly uniform angular spectrum of illumination, low vibration, low electrical noise and an intensity of illumination that allows for a good signal-to-noise ratio in the images obtained by IR analog detector 110, one can achieve a standard deviation of the birefringence measurement that is smaller than the birefringence resolution, particularly with the use of signal processing as described below.

On the other hand, were system 10 to have a non-uniform angular spectrum of illumination, a poor signal-to-noise ratio in the images or substantial speckle, the standard deviation of the birefringence measurement could significantly exceed the birefringence resolution of the system, sometimes by nearly an entire order of magnitude.

When using a relatively broadband light source 60, such as an LED or a light bulb, the aforementioned optical filter 66 (e.g., a band-pass optical filter, a low-pass optical filter, or a high-pass optical filter) can be employed to reduce the bandwidth of the illumination and improve the sharpness of the TIR/PR transition. For example, when the wavelength spectrum of the 1,550 nm LED is too great, for example, greater than about 50 nm at FWHM, such filtering can improve the performance of system 10. The same optical filter 66 can also reduce noise or unwanted erroneous background signal from ambient light.

Sample measurements were performed using an example system 10 configured with light source 60 having an ASE source based on an erbium-doped fiber amplifier (EDFA). This source 60 was used because of its well-defined output mode and because of its relatively high output power compared to the available LED at 1,550 nm. While the typical power of a nominally 1,550 nm LED is on the order of 1-2 mW, the power of the EDFA-ASE source centered near the same wavelength can exceed 30 mW. Furthermore, the spectral brightness of the ASE source is further increased in comparison with that of the LED due to the significant difference in the spectral bandwidth.

Figure 6:
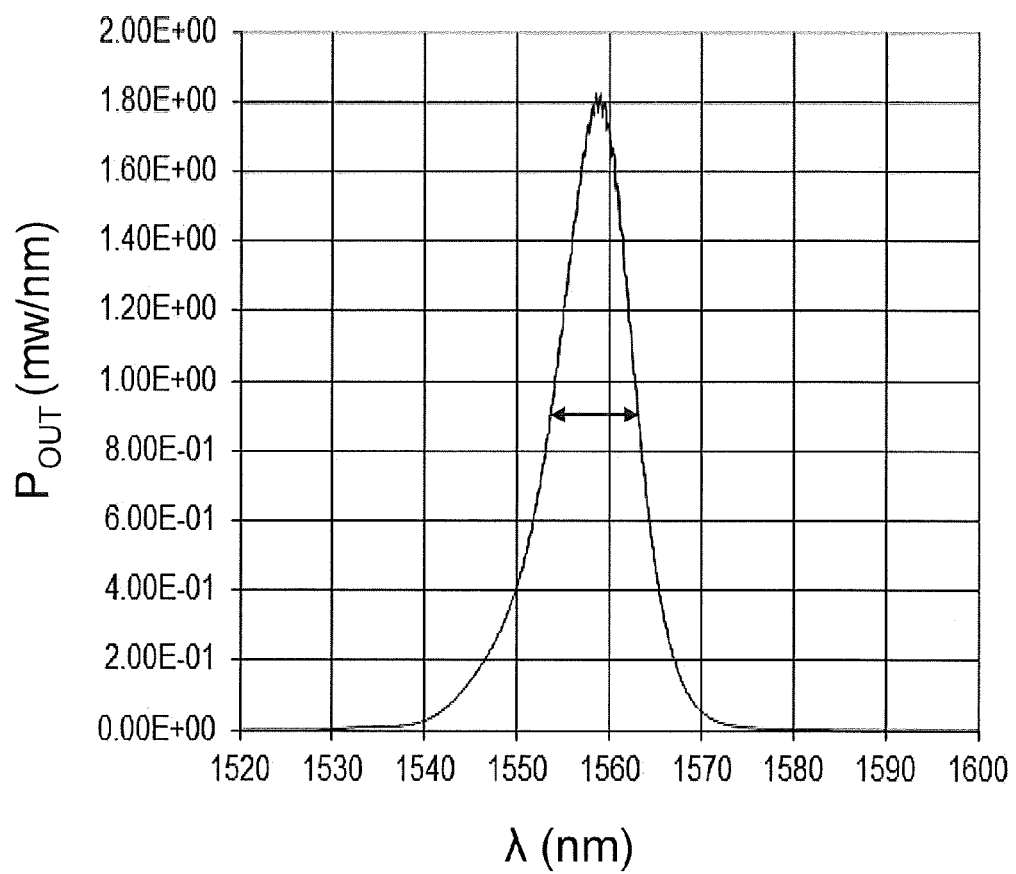
FIG. 6 is a plot of output power density (mW/nm) versus wavelength (nm) for a typical ASE source, and shows a bandwidth at full-width half-maximum (FWHM) of about 9 nm.

The typical spectral bandwidth of a 1,550 nm-LED source is about 100 nm at FWHM. FIG. 6 is a plot of output power spectral density $P_{OUT}$ (mw/nm) versus wavelength (nm) for a typical ASE source. The FWHM bandwidth of this source is about 9 nm for pump-laser-diode currents below about 150 mA. At higher currents, the onset of laser oscillations is observed, which narrows the spectrum. The EDFA-ASE fiber light source 60 was operated at a pump-laser-diode current of 48 mA, where the output power of the EDFA is significantly smaller than 30 mW, but the power spectral density is still substantially higher than that of a 2-mW, 1,550 nm-LED source.

The EDFA-ASE fiber light source 60 emitted light 62 with the output spectrum of FIG. 6. The light 62 was made incident upon moving light-scattering element 70, which was formed from a thin round plastic sheet with micro-crystals on its surface. The typical crystal size was about 30-35 micrometers. The discoid light-scattering element 70 was mounted on a small motor in such a way that the light beam 62 was passing through the plastic sheet, and continuously spun to provide substantially uncorrelated speckle patterns at different moments in time. The images captured by photodetector system 130 were time averaged, i.e., the different images with different speckle patterns were added up (summed) in order to mitigate speckle and obtain substantially speckle-free average images.

Depending on the image-capture time and the speed of movement light-scattering element 70, partial or even significant speckle reduction may be seen even with a single image, when many substantially uncorrelated speckle patterns are formed within a single image-capture time. In the described experiment, the image-capture time was fixed by the equipment, and averaging multiple images was found effective to substantially reduce speckle beyond the partial reduction in a single image.

It was also observed that a moving light-scattering element 70 with a typical crystal size of 15 microns was also effective in reducing the speckle with our ASE source with a wavelength near 1,550 nm and a bandwidth of about 9 nm, while moving light-scattering elements 70 with crystal sizes of 6 microns and smaller were not as effective.

For system 10 operating at wavelength λ, a moving light-scattering element 70 with a grit size greater than about 5λ, or in another example greater than about 10×, is effective in suppressing speckle for the purposes of surface birefringence measurement in strongly attenuating samples 20.

Having a static light-scattering surface on optical axis A1 (e.g., light-scattering portion 43) on input surface 42 of coupling prism 40 or close to the coupling prism (e.g., in focusing optical system 80 or between the coupling prism and optical system 80) reduces intensity losses due to the scattering of light outside of the numerical aperture of collecting optical system 90 more than is the case when a static light-scattering element 70 is disposed closer to the light source. In addition, with only a moderately scattering and moving light-scattering element 70 and a light-scattering portion 43 disposed on coupling prism input surface 42, most of focused light 62F can be converged onto a spot of desired size at input surface 42, thereby reducing the amount of stray light that might make its way to photodetector system 130. An example spot size is between ¼ and ⅔ of the full length of interface 50 when the prism cross-section in the plane of the figure is an isosceles triangle.

Utilizing a light-blocking portion on output surface 46 helps block unwanted stray light produced by scattering portion 43 of prism input surface 42 from reaching IR analog detector 110. Static diffusing surfaces designed to smooth the uniformity of angular distribution can be selected to have surface bumps or pits at an average spacing of 30-60 wavelengths. If substantial broadening of the angular distribution is also desirable, bumps and pits with a broad distribution of sizes and spacings may be utilized, including a substantial portion of such features spaced apart by as few as 4 wavelengths. Diffusing surfaces with such properties may be obtained by sandblasting or other surface roughening techniques.

In a related aspect of the disclosure, stray light at photodetector system 130 is reduced by coating one or more of the unused surfaces of coupling prism 40, e.g., surfaces other than coupling surface 44 and input and output surfaces 42 and 46, by an absorbing coating 49 (see FIG. 5, which shows a portion of an example absorbing coating). In an example, absorbing coating 49 has a refractive index $n_A$ similar to or higher than the refractive index $n_p$ of coupling prism 40. In one example, the refractive index $n_A$ of absorbing coating 49 at the operating wavelength λ satisfies $n_A > n_p - 0.1$, while in another example it satisfies $n_A > n_p - 0.02$. In addition, absorbing coating 49 has significant absorption at the operating wavelength λ, in one example being greater than about 100 dB/mm, and in another example being greater than about 1,000 dB/mm.

In an example, coupling prism 40 is made of F2 (Schott) glass with a refractive index $n_p$ of about 1.595 near λ=1,550 nm, and one or more of the unused sides is dip-coated or spin-coated with photoresists to form absorbing coating 49. Prior to depositing absorbing coating 49 on coupling prism 40, carbon micro-particles or nano-particles are dissolved in the photoresist to increase absorption.

In an example, a carbon paste or carbon suspension in isopropanol may be mixed with the photoresist to form the material for absorbing coating 49. The volume of carbon paste or suspension is desirably greater than about 2% of the volume of the photoresist. In addition, the mass of the carbon without the suspension solvent is desirably less than about 30% of the mass of the photoresist.

After curing, photoresist-based absorbing coating 49 has a refractive index $n_A$ of about 1.6, which is close to the refractive index $n_p$ of coupling prism 40. An example photoresist includes any photoresist of the Shipley 1800 series, such as S1813 or S1827, and the mass of the carbon without suspension solvent is about 5-10% of the mass of the photoresist.

An example operation of system 10 to carry out the method of measuring birefringence in top surface 24 of sample 20 is now described. In an example, a calibration or reference measurement is taken with light source 60 illuminating coupling prism 40 when sample 20 is absent, i.e., when there is vacuum, air, nitrogen, or other nonreactive gas adjacent coupling-prism coupling surface 44. This provides a reference reading for sections 112TE and 112TM of photosensitive surface 112 of IR analog detector 110.

The photodetector system 130 may be limited in its collection time per image for a single frame (an example time is 1/30 of a second for frame grabber 120). Thus, in an example embodiment, multiple frames (images) are collected and then averaged to reduce speckle and improve the signal-to-noise ratio. An example frame averaging is 25 frames collected at a frame capture rate of 8 frames per second (fps). In an example, the frame capture rate is dictated by the speed of moving light-scattering element 70 to ensure that different captured frames contain substantially uncorrelated speckle patterns.

In one example configuration of system 10, collecting optical system 90 had a focal length f=75 mm, and photosensitive surface 112 of IR analog detector 110 had a width in the x-direction of 12.7 mm, which supported an angular spectral range of about 9.7° around a central angle $\beta_2$ of about 22.9°. For a coupling prism refractive index $n_p$=1.5948 at 1,550 nm, this exit-angle range corresponds to a range of about 6.1° around a central incidence angle θ on the inside of coupling prism 40 of about 74.1°.

When only air is in contact with coupling surface 44 of coupling prism 40, TIR is usually observed at all angles within the range imaged onto photosensitive surface 112. Thus, the captured calibration (reference) image represents the angular distribution of illumination of coupling surface 44 of coupling prism 40. This calibration angular spectrum is used to normalize the raw TE and TM angular spectra obtained when top surface 24 of sample 20 is in contact with coupling surface 44 of coupling prism 40 to form interface 50. This normalization involved dividing the raw TM and TE spectra by the "reference" TM and TE angular spectra.

Some amount of ambient light may enter coupling prism 40 from coupling surface 44 through refraction, and reach the photodetector system 130, thereby contributing an unwanted component in the reference signal. Hence, in an example embodiment, light source 60 emits light 62 that is significantly brighter than any ambient light. In another example, coupling prism 40 includes the aforementioned light-blocking members 45.

When sample 20 and coupling prism 40 are properly interfaced, photodetector system 130 records the TE and TM angular reflection/coupling spectra simultaneously. This provides raw measured TE and TM angular spectra. As in the aforementioned calibration step, in an example, multiple captured images (frames) are averaged, e.g., 25 frames collected at 8 fps. In an alternative embodiment, the TE and TM angular spectra may be sequentially recorded using a single polarizer that is rotated appropriately between each recording of TE and TM spectra.

The TE and TM spectra differ in part due to the different boundary conditions for TE and TM waves at prism-sample (or oil-sample) interface 50; in addition, the two spectra are offset from each other based on the amount of birefringence associated with the surface stress in sample 20. However, in practice, the two spectra have additional differences that arise, for example, due to noise in system 10, different background noise for photosensitive surface 112, the non-uniformity of focused light 62F, the non-uniform reflectance (for example, at output surface 46 of coupling prism 40) of reflected light 62R, and significant light scattering in substrate 20 that may depend on polarization and angle.

Thus, an aspect of the method of measuring the surface stress in sample 20 involves processing the TE and TM angular spectra to remove the various differences between them so that they come to resemble each other as closely as is possible without altering the fidelity of the data.

To this end, the TE and TM raw spectra are divided by the corresponding reference TE and TM spectra to yield normalized TE and TM spectra, i.e., a normalized image. If camera 110 has nonlinear response, then the non-linear response is usually described by parameter γ defined by $(I_2/I_1)^\gamma = V_{s2} N_{s1}$, where $I_1$ and $I_2$ are different optical intensity levels incident on the camera, and $V_{s1}$ and $V_{s2}$ are the corresponding levels of the analog video signal produced by the camera in response to these incident intensities.

Figure 7:
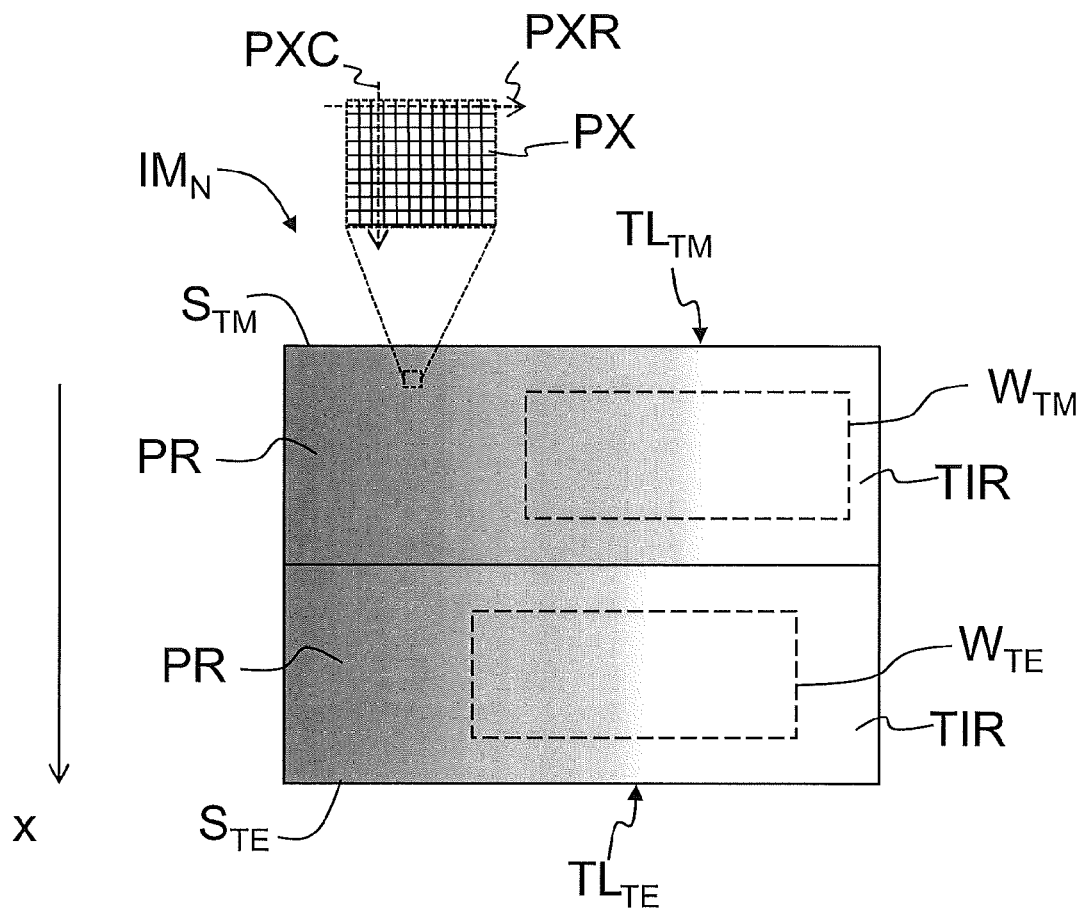
FIG. 7 is a schematic representation of a normalized image $IM_N$ that shows the normalized TE and TM angular reflectivity spectra $S_{TE}$ and $S_{TM}$ associated with the top and bottom parts of the image, respectively.

In such cases of nonlinear response, the proper way to apply the normalization is by following the equation $IM_N = (IM_{samp}/IM_{ref})^{1/\gamma}$, where $IM_N$ is the normalized image, $IM_{samp}$ is the image taken in the presence of sample 20, and $IM_{ref}$ is the reference image taken in the absence of the sample. Even when no reference image is taken, the same formula can be used for normalization of the sample image, taking the form $IM_N = IM_{samp}^{1/\gamma}$. FIG. 7 is a schematic representation of a normalized image $IM_N$ that shows the normalized TE and TM spectra $S_{TE}$ and $S_{TM}$ on the bottom and top parts of the image, respectively. An example dimension of normalized image $IM_N$ when using IR analog detector 110 is 480 rows and 640 columns of square pixels that are about 19.8 microns on a side.

The normalized image of $IM_N$ has a bright band of total internal reflection TIR in the right-hand-side portion, while a darker band of partial reflection PR is observed on the left-hand-side portion. In a different configuration wherein IR analog detector 110 is rotated 180° around optical axis A2, which connects the camera and the lens, or wherein the camera internal beam or logic is scanning the image in the opposite direction of subsequent image reproduction, the opposite case may be observed, with the left-hand-side of the image being the bright band TIR, and the right-hand-side being the darker band of partial reflection PR.

A significant shift is observed between the general locations $TL_{TM}$ and $TL_{TE}$ of the TIR/PR transition for the normalized TE and TM angular spectra $S_{TE}$ and $S_{TM}$. The precise measurement of the difference in position of the TIR/PR transition represents the difference $\Delta\theta_C = \theta_{C-TE} - \theta_{C-TM}$ between the TE and TM critical angles, which allows for a precise estimate of the birefringence in sample 20. The normalization of the TE and TM spectra reduces or eliminates artifacts in the raw TE and TM spectra that can arise from a non-uniform angular distribution of the illumination intensity of focused/angularly dispersed light 62F.

FIG. 7 shows sub-regions or cropping windows $W_{TE}$ and $W_{TM}$ within the respective normalized TE and TM angular spectra $S_{TE}$ and $S_{TM}$. A close-up view of example pixels PX is shown. Pixel rows PXR run horizontally within each window and pixel columns PXC run vertically. The pixel rows PXR are added up (summed) for each of the normalized TE and TM angular spectra to produce a single signal for each spectrum that is then normalized by the maximum intensity. The result represents an average angular distribution for the given spectrum as represented as intensity versus pixel column number. This yields normalized and averaged TE and TM spectra.

Even when the captured images that went into forming normalized image $IM_N$ were generated by IR analog detector (camera) 110, they are captured and stored in a pixel matrix format by digitizing frame grabber 120. In the example of FIG. 7, the TE cropping window $W_{TE}$ is shifted to the left by 20 pixels with regard to the TM cropping window $W_{TM}$ in order to approximately compensate in advance for an expected amount of birefringence. Doing so better captures the TIR/PR transition locations $TL_{TM}$ and $TL_{TE}$ in the middle of each cropping window.

Figure 8A:
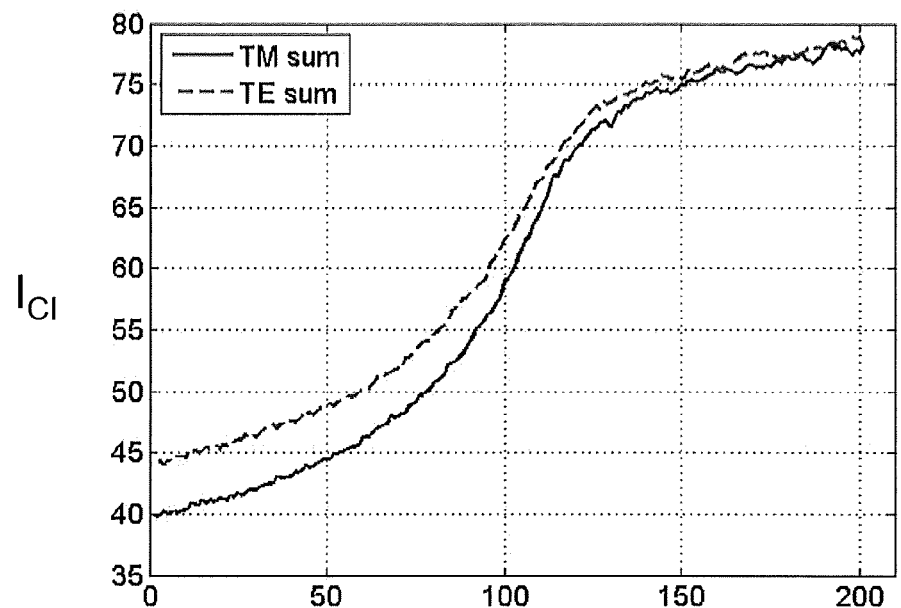
FIG. 8A is a plot of the summed column intensity versus pixel column and shows the normalized and averaged TE and TM spectra (dashed and solid lines, respectively)

FIG. 8A is a plot of the summed column intensity $I_Q$ versus pixel column PXC within the cropping window and shows the normalized and averaged TE and TM spectra (dashed and solid lines, respectively). The shift of the TE window $W_{TE}$ with respect to the TM window $W_{TM}$ has not been taken into account. It is added later in the final calculation of birefringence after overlapping the two fully processed intensity distributions. Note that the number of pixel columns PXC in FIG. 8A and other Figures is the same as the number of pixels PX in a single pixel row (line) PXR, since the rows have been averaged.

The two curves of FIG. 8A differ significantly in shape, in large part due to the different boundary conditions for the TE and TM waves, as mentioned above. In the presence of strong scattering, this difference in boundary condition may also result in a difference in the scattered light distribution for the two polarizations, leading the two curves to become additionally and differently distorted.

Interchanging the order of row summation and normalization to the non-sample intensity distribution is expected to preserve the capability of the overall data processing to extract precise and reliable values of the birefringence and associated surface stress. In particular, areas of summation can be identified for TE and TM spectra and applied to both the sample image and the reference (calibration) image. Summation can be performed in the sample angular spectrum and in the reference angular spectrum, and then the summed spectra within the windows can be divided, e.g., the summed sample spectrum divided by the summed reference spectrum, to obtain the distributions of TM and TE summed column intensities $I_{CI}$ of FIG. 8A.

Figure 8B:
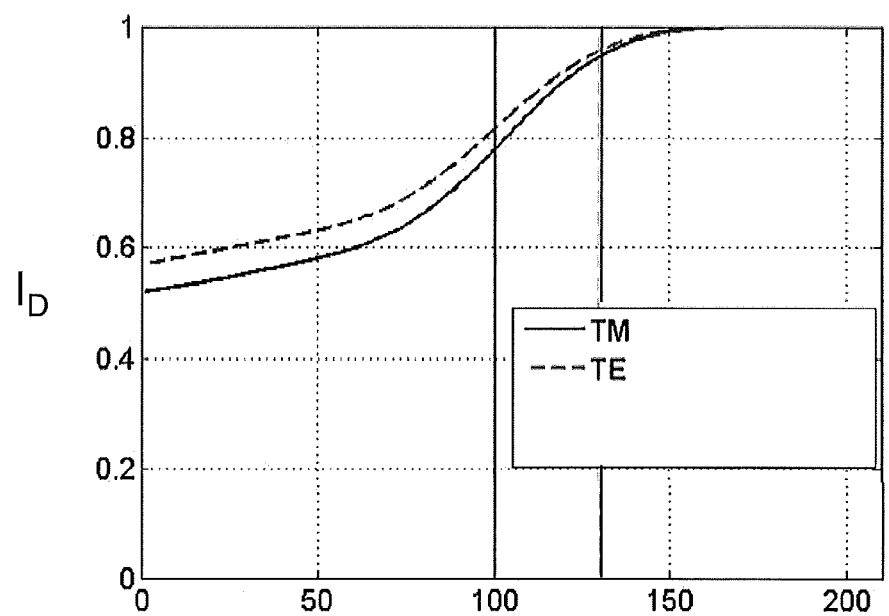
FIG. 8B is similar to FIG. 8A and shows the angular column intensity distributions after having been low-pass filtered to reduce noise, as well as normalized to their respective maxima.

FIG. 8B is similar to FIG. 8A and plots $I_D$ versus pixel column PXC, where $I_D$ represents the distributions of the angular column intensities $I_Q$ after being low-pass filtered to reduce noise and normalized by being divided by their respective maxima. The difference in shape due to the different boundary conditions for TE and TM waves persists in these smoothed and normalized signals. The solid vertical lines in the plot represent the boundary of the comparison region used in this particular example for determination of the mutual shift, as explained below.

Figure 8C:
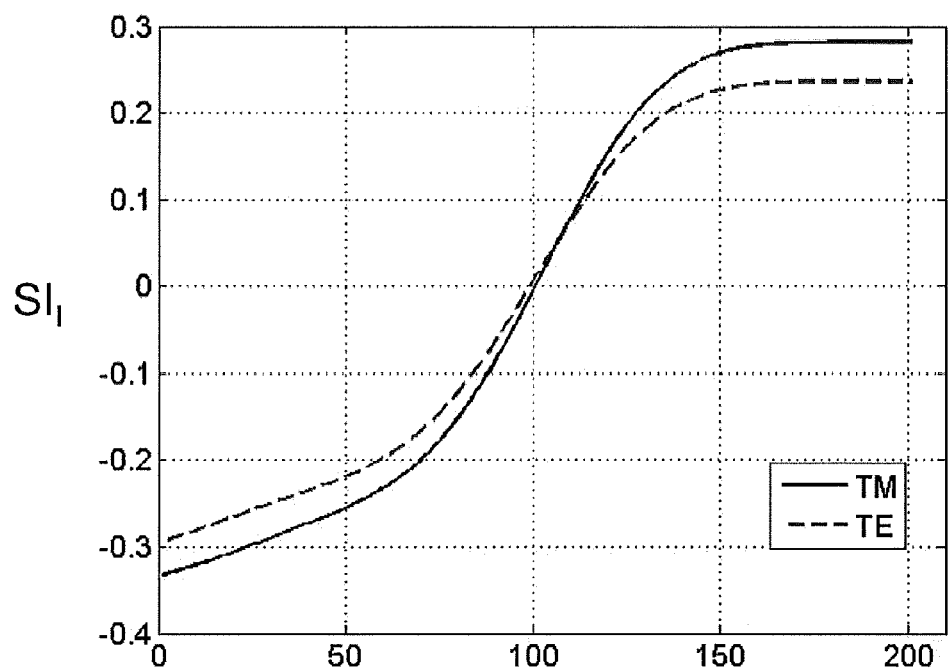
FIG. 8C is similar to FIG. 8B and shows initial contrast signals for the TM and TE polarizations obtained by dividing the low-pass filtered and normalized intensities of FIG. 8B by their respective angular averages.

FIG. 8C is similar to FIG. 8B and shows initial contrast signals $SI_I$ for TM and TE polarizations, which are obtained by dividing the low-pass filtered and normalized column intensities $I_D$ of FIG. 8B by their respective angular averages and then subtracting 1, namely, contrast signal $SI_I$ equals the difference between the signal and the average, divided by the average. The two contrast signals $SI_I$ may have somewhat different contrast ranges, which is not ideal for their direct comparison. Note that the step of normalizing to maximum intensity in the preparation of the signal of FIG. 8B as described in the previous paragraph may be omitted in actual signal processing if normalization to the angular average intensity is performed for each signal, as in the preparation of FIG. 8C.

Figure 8D:
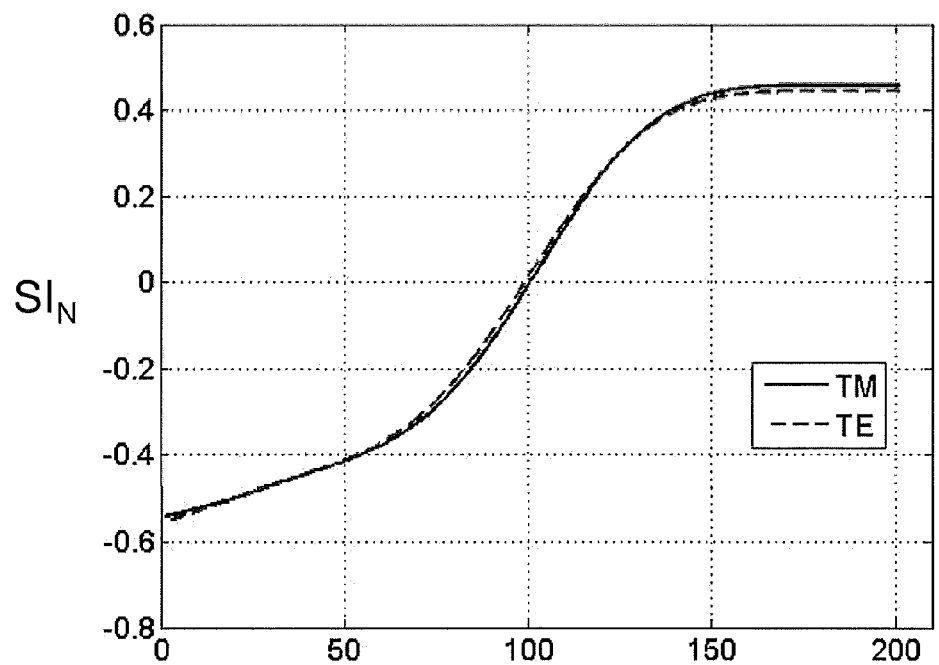
FIG. 8D is similar to FIG. 8C and shows the TE and TM contrast signals of FIG. 8C after being normalized to their respective total intensity ranges.

FIG. 8D is similar to FIG. 8C and shows the TE and TM contrast signals of FIG. 8C after being normalized by being divided by their respective total intensity ranges. These signals are denoted $SI_N$. At this point, both TE and TM contrast signals cover a vertical range of unit size, but the centers of the two ranges may be shifted slightly vertically with respect to each other.

Figure 8E:
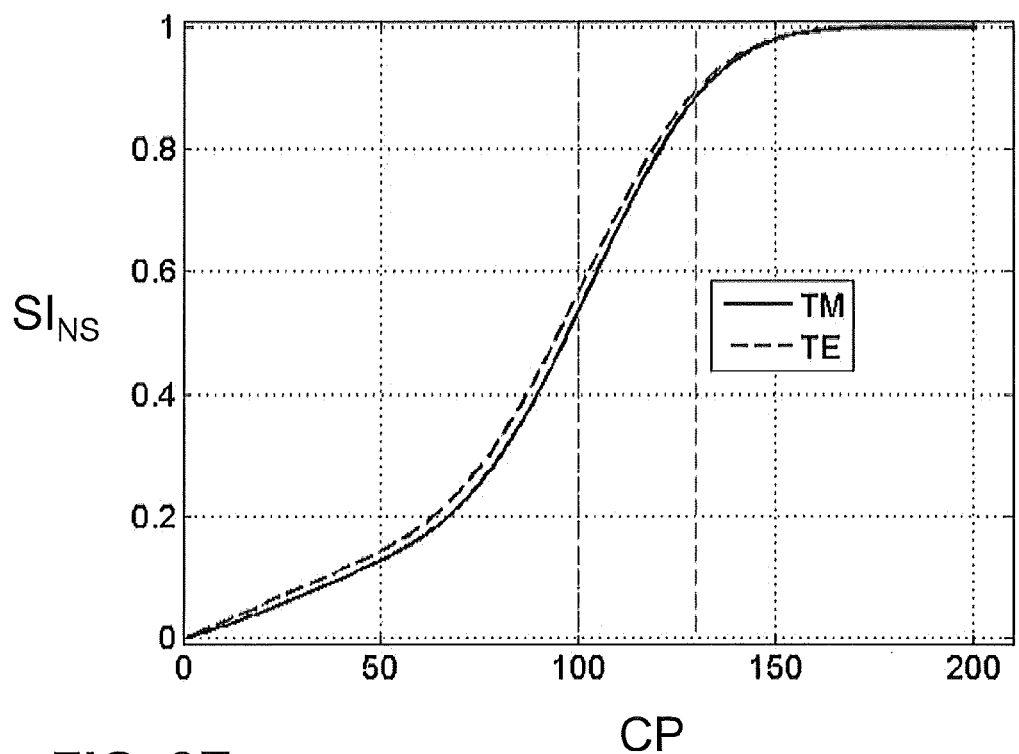
FIG. 8E is similar to FIG. 8D and shows the normalized contrast signals of FIG. 8D after their being shifted to a common point, which in the example is the point of maximum intensity in the contrast signal as shifted to the value 1 for each signal.

FIG. 8E is similar to FIG. 8D and shows the normalized contrast signals of FIG. 8D after being shifted to a common point, which in the example is the point of maximum intensity in the contrast signal as shifted to the value 1 for each signal. These normalized and shifted signals are denoted $SI_{NS}$. Thus, in the present example, both the TE and TM contrast signals share identical ranges 0 to 1, making it easier to compare the two signals and thereby determine the mutual angular shift.

After the above-described contrast formation and normalization procedures have been performed, the TE and TM contrast signals are almost identical in shape, as is evident from FIG. 8E. Obtaining the birefringence is now accomplished by performing a lateral shift until the two contrast curves are optimally aligned within a chosen region of steep change.

Figure 8F:
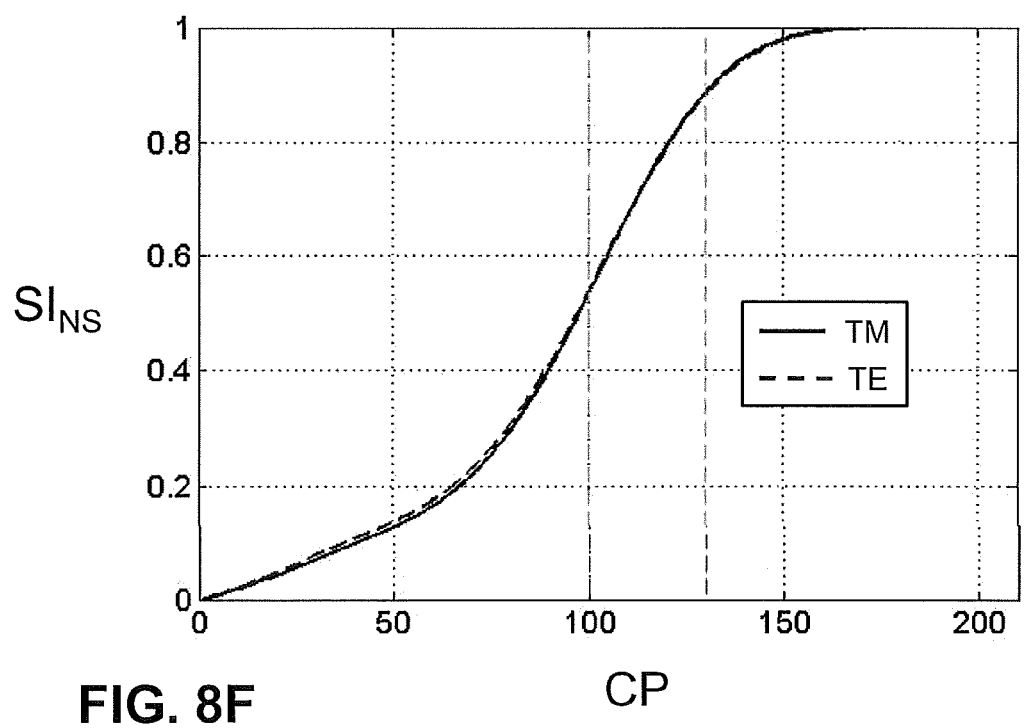
FIG. 8F shows normalized contrast signals for TE and TM polarization overlapped within the comparison region (in the example, pixel columns 100 through 130) by horizontally shifting the TE contrast signal.

FIG. 8F shows normalized and shifted contrast signals $SI_{NS}$ for TE and TM polarization as overlapping within the comparison region (pixel columns 100 through 130, in this example), which was obtained by horizontally shifting the TE contrast signal. The comparison region was selected to align the two signals in a steep portion of the intensity transition, and more specifically in the top half of the steep portion. This region corresponds to effective index values that are very close to the value representing the edge of TIR and the critical angle. This region corresponds to TIR angles that are only slightly larger than the ETIR, and is closely related to the surface refractive index of sample top surface 24 when the characteristic depth of the refractive index distribution in the sample is substantially larger than the penetration depth of the exponentially decaying field.

In another embodiment, the shift between TE and TM signals can be determined by centroid method, which finds the geometric center of the derivatives of reflectivity $dR/d\theta$. Although the geometric center is not necessarily located at the spectral position of the maximum reflectivity derivative (the curve is typically asymmetrical as shown in FIG. 3B), the offset of the geometric center does not affect the final measurements. The centroid algorithm, which is applied to pixels with values falling below the threshold value xthresh, yields the centroid value $C=sum(i*(xthresh-xi))/sum(xthresh-xi)$, where xi is the value of derivative at pixel i, xthresh is the threshold of derivative which is determined by the noise level of the centroid output. A lower threshold value will generally reduce the centroid noise by including more pixels in the calculation.

It has been recognized that over a wide range of substrate attenuation and the refractive indices of coupling prisms 40 and substrates 20, the location at which the transition signal for each polarization undergoes the steepest change occurs within less than 0.1° of the critical angle that corresponds to the case without attenuation. In addition, it has been recognized that when the effects of scattered light are neglected, the location of steepest change for the TM light differs only negligibly from that for the TE light when the near-surface region of substrate 20 is not birefringent.

Hence, it is likely that the comparison of the TE and TM signals would yield the most accurate estimate of birefringence and stress when the comparison region is centered on the angle of steepest change, e.g., the maximum absolute value of the derivative of the transition signal. Precise and accurate measurements of birefringence and surface stress are possible if the comparison region is a subset of normalized contrast signal $SI_N$, which in one example lies between levels of about 0.15 and about 0.90, and in another example lies between 0.20 and 0.85, and a subset covering a normalized-contrast vertical range that in one example is greater than about 0.05 and in another example is greater than 0.1. It is also clear from FIG. 8F that the slope of the final normalized signals $SI_N$ in the selected comparison region is similar to the maximum slope of the signal, and in one embodiment is than 40% of the maximum slope or greater and in another example is about 70% of the maximum slope or greater.

A shift of 1.9 pixels PX was found to optimally align the TE and TM normalized contrast curves in the comparison region shown in FIG. 8F. This shift is added to the 20-pixel initial shift of the TE window $W_{TE}$ relative to TM window $W_{TM}$, for a total birefringence measurement of 21.9 pixels PX. The pixel width for 640×480 pixel images obtained with a 12.7 mm-wide IR analog detector is 19.8 μm. The effective-index resolution corresponding to 1 pixel PX (eq. (5)) is 0.0000687, so the calculated birefringence is (21.9 pixels)×(0.0000687)= 0.001505.

This measured surface birefringence is converted to surface stress by dividing the value by the stress-optic coefficient (SOC). The SOC of glasses with compositions similar to that of the white glass-ceramic used in the described experiment typically ranges between $1.5 \times 10^{-6}$ and $3.5 \times 10^{-6}$ RIU/MPa. The SOC of the particular glass-ceramic used herein was measured separately once by first measuring (using the described method) the stress-induced surface birefringence of two series of samples having two substantially different levels of surface stress as a result of their having been prepared under two different ion-exchange conditions.

The samples were then subjected to destructive one-side etching, and measurements of their curvature as a result of the disturbed force balance due to asymmetric stress distribution were used to calculate the actual stress profiles using a known Young's modulus for the material. Eventually, by comparing the results of the birefringence measurements with the stress profiles inferred from the etching measurements, an SOC of $2.5 \times 10^{-6}$ RIU/MPa was determined. Using this SOC, the surface stress of sample 20 described in the present example is 602 MPa.

Based on multiple measurements on 12 nominally identical samples 20 of ion-exchanged white glass-ceramic, the standard deviation of the measurement was estimated to be about 0.000062 RIU, which is slightly smaller than the index resolution of 0.0000687 that corresponds to the width of one pixel in the angular spectral images. Part of the estimated standard deviation was likely due to real minor differences in stress between the nominally identical samples 20. In a different batch of 10 samples 20, a standard deviation of 0.000055 RIU was estimated. The true precision of the measurement for the considered opaque white glass-ceramic may be better than 0.00005 RIU and can be measured by performing a large number of measurements on a single sample 20.

Measurements of a sample 20 of white glass ceramic 18 times with system 10 were carried out in an example system 10 in which background from scattered and ambient light controlled, The length of coupling prism 40 was 25 mm instead of 15 mm, and the focal length of collection lens 90 was 100 mm instead of 75 mm. A measurement standard deviation of $1.61 \times 10^{-5}$ RIU was obtained during measurements of birefringence, with an average value of $1.21 \times 10^{-3}$ RIU. In this particular case, the standard deviation represents 1.3% of the average.

For some materials with lower attenuation at the measurement wavelength, an even smaller standard deviation may be possible.

Thus, the above example method of measuring the surface stress is summarized by the following steps:

1. Capture calibration/reference image(s) of TE and TM angular spectra via coupling-prism coupling surface 44 without sample 20 present to obtain calibration intensity data. If necessary, correct for small azimuthal misalignment between sensor frame and prism output surface 46 frame by a minor rotation of the image, which can be performed by software.
2. Capture image(s) of TE and TM TIR spectra via prism coupling with top surface 24 of sample 20. Rotate image if necessary.
3. Normalize measured TE and TM angular reflection spectra of sample 20 to TIR spectra without the sample by dividing the TE and TM spectra with the sample by the TE and TM spectra without the sample and correcting for the camera nonlinearity (if present) by raising the ratio to the power of $1/\gamma$. If normalization to a reference spectrum is not used, but camera 110 has nonlinear response, then the image of the TE and TM spectra can be normalized by correcting for the camera's nonlinearity, thereby raising the raw image to the power of $1/\gamma$. Steps 1 and 3 are not absolutely necessary but often improve the measurement precision.
4. Select cropping windows $W_{TE}$ and $W_{TM}$ for TE and TM spectra that define a subset for each of the TE and TM spectra. Sum the image rows within the cropping windows. If the windows have different number of rows, the summed signals may be divided by the number of rows to compare signal per row. One window may be shifted with respect to the other based on an initial guess about the amount of birefringence.
5. Low-pass filter the summed spectra and optionally divide the filtered spectra by their respective maxima to obtain filtered, optionally normalized TE and TM spectra $LPF_{TE}$ and $LPF_{TM}$.
6. Calculate average intensity $I_{ATE}$ and $I_{ATM}$ for TE and TM spectra $LPF_{TE}$ and $LPF_{TM}$.
7. Calculate TE contrast $C_{TE}=(LPF_{TE}-I_{ATE})/I_{ATE}$ and TM contrast $C_{TM}=(LPF_{TM}-I_{ATM})/I_{ATM}$
8. For each polarization, calculate a normalized contrast signal CN, i.e.:

$$CN_{TE}=C_{TE}/(\max(C_{TE})-\min(C_{TE})) \text{ and } CN_{TM}=C_{TM}/(\max(C_{TM})-\min(C_{TM}))$$

9. For each polarization, establish a common maximum CM or common minimum CMin for each normalized contrast, and calculate a final normalized contrast CFN for each polarization, namely:

$$CFN_{TE}=CN_{TE}+CM-\max(CN_{TE}) \text{ and } CFN_{TM}=CN_{TM}+CM-\max(CN_{TM})$$

or alternatively, $$CFN_{TE}=CN_{TE}+CMin-\min(CN_{TE}) \text{ and } CFN_{TM}=CN_{TM}+CMin-\min(CN_{TM})$$

10. Determine the horizontal or angular shift between the final normalized contrasts $CFN_{TE}$ and $CFN_{TM}$ that provides the best (optimal) overlap between the two in a steep portion of the high-intensity-to-low-intensity transition. In an example, the comparison region for the two spectra includes the maximum slopes for each spectrum (CFN signals). In an example, the region of comparison is defined as that portion of the spectra where the slope of the CFN signal is larger than about 70% of the maximum slope of the CFN signal. In another example, the region is defined as that portion of the spectra where the slope of the CFN signal is larger than about 50% of the maximum slope of the CFN signal. In an example, the comparison region that includes the maximum slope is selected to include two levels of the CFN signal that are identical for both the $CFN_{TE}$ signal and the $CFN_{TM}$ signals. The shift that minimizes the difference between the final normalized contrasts $CFN_{TE}$ and $CFN_{TM}$, added to the initial mutual horizontal displacement of the cropping windows, is the estimate of surface birefringence B when expressed in refractive index units using a formula which may be specific to the system used for obtaining a representation of the angular reflectivity spectrum.

11. If necessary, apply a correction factor on the order of 1 (e.g., between 0.9 and 1.1) to convert the measured birefringence to an estimate of surface birefringence B.
12. Calculate the stress from surface birefringence $\sigma = B \cdot SOC$, where SOC is the stress-optic coefficient for sample 20.

In another embodiment, the method of measuring the surface stress is summarized by the following steps, with the first four steps (not listed below) being the same as in the above method:

1. Low-pass filter the summed spectra to obtain filtered, optionally normalized $LPF_{TE}$ and $LPF_{TM}$;
2. Band-pass filter the summed spectra to obtain band-pass filtered $BPF_{TE}$ and $BPF_{TM}$.
3. Take a ratio of the band-pass to the low-pass filtered signal for each polarization;
4. For each polarization subtract the minimum signal so that the minimum signal is now zero.
5. For each polarization, divide the new signal by the maximum so now the signal for each filtered polarization is between 0 and 1 and is normalized as contrast.
6. Shift the final contrast curve of one polarization longitudinally with respect to the curve of the other polarization until the best overlap between the two is obtained within a pre-selected window (typically containing the steepest portion of the high-intensity-to-low-intensity transition). The shift that minimizes the difference is the estimate of surface birefringence B when expressed in refractive index units using a formula which may be specific to the system used for obtaining a representation of the angular reflectivity spectrum.
7. If necessary, apply a correction factor to convert the measured birefringence to estimate of surface birefringence B.
8. Calculate the stress from surface birefringence B via $\sigma = B \cdot SOC$, where SOC is the stress-optic coefficient for sample 20.

In another embodiment, the position of the maximum derivative of the reflected intensity is used to accurately estimate surface birefringence B and stress. The first 5 steps (not listed below) are the same as in the previous two methods.

1. Calculate the numerical derivative signal for each of the low-pass-filtered TE and TM signals.
2. Interpolate the two numerical derivative signals on a denser 1-dimensional mesh with a point spacing smaller than the pixel spacing to find the position of the derivative maxima with sub-pixel precision. Alternatively, for each of the two derivative signals, obtain a quadratic or other single-peak-function fit for the derivative signal in a narrow region around the maximum, and calculate a more precise position of the maximum of the fitting function with sub-pixel precision.
3. Find the difference between the positions of the fitted or interpolated maxima with sub-pixel resolution.
4. Add the value of the mutual shift between the TE and TM cropping windows to the difference found in the previous step to obtain the total shift with sub-pixel resolution. The total shift, multiplied by the index resolution per pixel PX, is the estimate of surface birefringence B.

The index resolution per pixel PX may be specific to the system used for obtaining a representation of the angular reflectivity spectrum.

5. If necessary, apply a correction factor to convert the measured birefringence to the estimate of surface birefringence B.
6. Calculate the stress from surface birefringence B via $\sigma = B \cdot SOC$, where SOC is the stress-optic coefficient for the sample.

The effect of strong optical attenuation on the sharpness of the reflectivity transition in the vicinity of the ETIR may depend on the penetration depth of the evanescent field inside sample 20 at TIR angles near the critical angle $\theta_C$ and the associated interaction distance of the light with the lossy sample. The critical angle $\theta_C$ is the launch angle $\theta = \theta_C$ corresponding to the ETIR. In a ray-optics approximation, a light ray that is totally internally reflected from coupling prism-sample interface 50 experiences a longitudinal shift parallel to the interface, namely, the aforementioned Goos-Hänchen shift. The interaction distance between light 62 and sample 20 is on the order of this shift.

For incidence angles $\theta > \theta_C$ that approach the critical angle $\theta_C$, the Goos-Hänchen shift for the TE polarization is well approximated by the equation $$S_{G-H}^{TE} \approx \frac{\lambda}{\pi n_p} \frac{\tan\theta_c}{\sqrt{\sin^2\theta - \sin^2\theta_c}} \quad (6)$$

and the corresponding expression for the Goos-Hänchen shift experienced by the TM-polarized light is $$S_{G-H}^{TE} \approx \frac{\lambda}{\pi n_p \sin(2\theta_c)} \frac{1}{\sqrt{\sin^2\theta - \sin^2\theta_c}} \quad (7)$$

Figure 9:
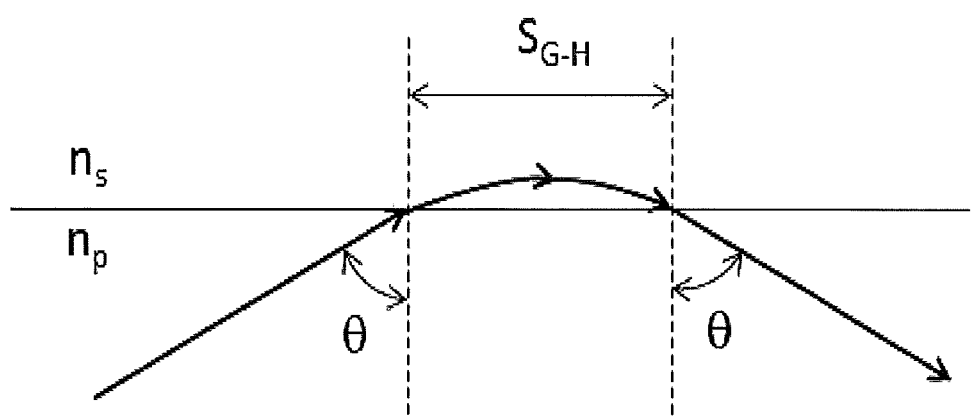
FIG. 9 is a schematic ray-optics diagram of the Goos-Hänchen shift $S_{G-H}$, with the sample on top and the coupling prism on the bottom, illustrating how the Goos-Hänchen shift defines the approximate interaction length.

FIG. 9 is a schematic ray-optics diagram of a Goos-Hänchen shift $S_{G-H}$, with sample 20 on the top and coupling prism 40 on the bottom. The incidence angle $\theta$ is slightly larger than the critical angle $\theta_C$ for total internal reflection.

Figure 10:
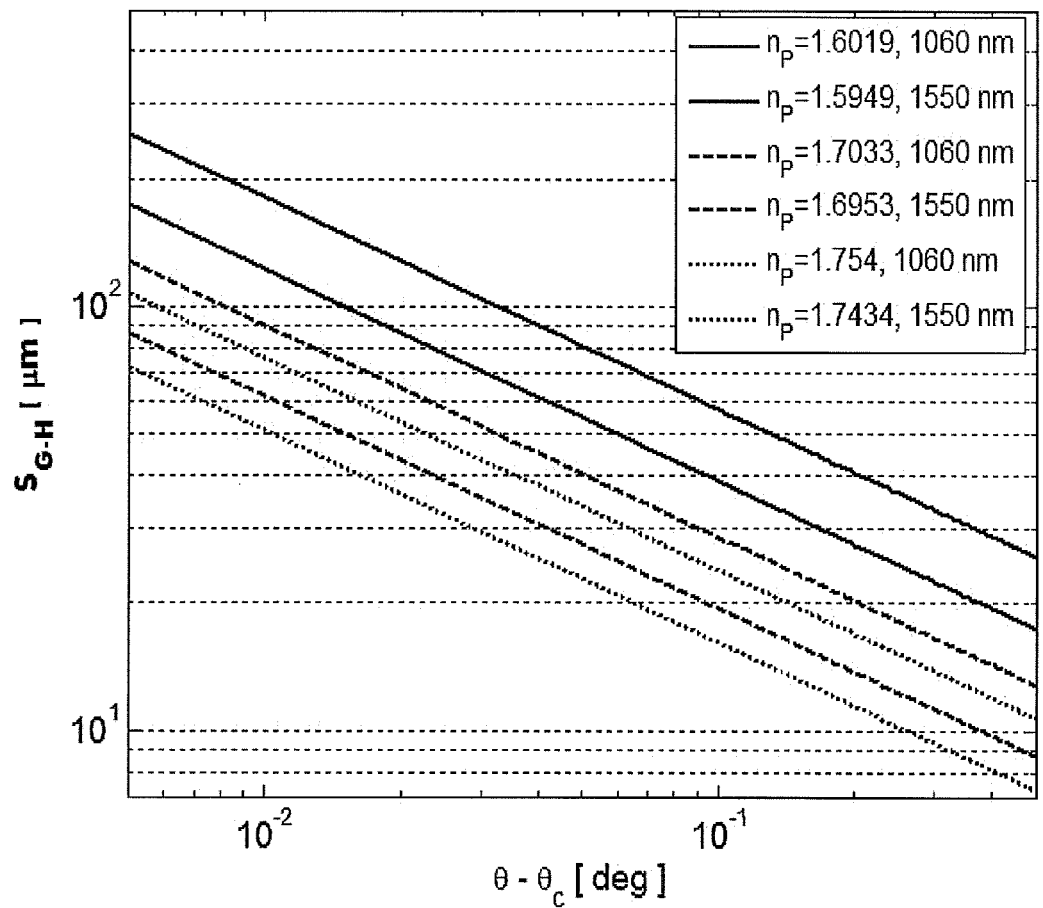
FIG. 10 is a plot of the Goos-Hänchen shift for TE-polarized light as a function of the deviation of the incidence angle from a critical angle $\theta_C$.

FIG. 10 is a plot of Goos-Hänchen shift $S_{G-H}$ for TE-polarized light as a function of the deviation of the incidence angle from critical angle $\theta_C$, according to equation (6). From equations (6) and (7), it is seen that Goos-Hänchen shift $S_{G-H}$ is proportional to the wavelength. Since the interaction distance between light 62 and sample 20 may be on the order of Goos-Hänchen shift $S_{G-H}$ in the ray-optics approximation, the reduction of reflection due to significant attenuation in the sample at shorter wavelengths at incidence angles larger than critical angle $\theta_C$ may be partially offset by the reduced interaction distance with the sample at shorter wavelengths.

In addition, if the total attenuation at near-critical angles $\theta_C$ is a major contributor to the broadening of the reflectivity transition, then attenuation data can be combined with calculations of Goos-Hänchen shift $S_{G-H}$ for different coupling prism indices $n_p$ and different operating wavelengths $\lambda$ to define specific configurations of system 10 with equivalent or improved performance at a new wavelength when experimental proof has been obtained of a system of adequate performance in birefringence measurements at that particular wavelength.

For example, a high-performance system 10 operating at 1,550 nm with a coupling prism index $n_p = 1.595$ for sample 20 with index $n_s$ of about 1.535 was formed. The pixel width of IR analog detector 110 was 19.8 µm and the focal length f of collecting optical system 90 was 75 mm. The attenuation for a white glass-ceramic at 1,550 nm was about 31 dB/mm, the effective index/birefringence resolution per pixel PX was about 0.000069 and $d\beta_2/dn_{\it eff}$=3.85 rad/RIU for a coupling prism angle α=60°.

A system 10 with equivalent performance but operating at 1,060 nm can be formed by taking into account the differences in attenuation, interaction length and sensitivity. Based on the attenuation data for the white glass-ceramic shown in FIG. 3, the attenuation at 1,060 nm in dB/mm can be estimated at about 3.5 times the attenuation at 1,550 nm.

To compensate for the larger attenuation, one can select coupling prism 40 to provide a shift at least 3.5 times smaller than the Goos-Hänchen shift $S_{G-H}$ near critical angle $\theta_C$ at an operating wavelength of λ=1,060 nm than coupling prism 40 with index $n_p$=1.595 produces at 1,550 nm. This condition is met by coupling prism 40 having a refractive index $n_p$ of about 1.75 and is substantially met by coupling prism 40 having a refractive index $n_p$≈1.7. The sensitivity $d\beta_2/dn_{\it eff}$ decreases significantly according to equation 3 for these higher-index coupling prisms 40.

However, this decrease in sensitivity can be compensated by one or more of the following: a) by using a higher-resolution IR analog detector 110 (especially if the new wavelength is shorter than 1,100 nm); b) by providing collecting optical system 90 with a longer focal length f; c) by increasing the numerical aperture of the collecting optical system or focusing optical system 80 if the resolution is limited by the aperture of either the illumination or the collection; d) by taking advantage of improved fundamental optical resolution at shorter wavelengths.

If the performance of system 10 is limited in the first place by the large breadth of the transition due to strong attenuation, combined with noise in the system, then presumably it is due to an excess of optical resolution. Thus, the focal length can be increased to compensate for decreased sensitivity $d\beta_2/dn_{\it eff}$.

CMOS and CCD cameras with sensitivity at wavelengths shorter than 1,100 nm and with pixel sizes in the range 3-6 µm are commercially available at significantly lower cost than cameras operating at 1,550 nm. Hence, if the precision is limited by the resolution of photodetector system 130, then the reduced angular sensitivity of coupling surface 44 of coupling prism 40 at 1,060 nm due to the use of a higher-index coupling prism can be compensated by the higher pixel resolution of the CMOS or CCD cameras operating at wavelengths below 1,100 nm.

Table 1 below shows the sensitivity $d\beta_2/dn_{\it eff}$ of the exit angle $\beta_2$ to change in the effective index of propagation $n_{\it eff}$ in sample 20 with refractive index $n_s$ of about 1.535 at 1550 nm, calculated for three coupling prisms 40 and two of the considered infrared wavelengths.

TABLE 1

| Coupling prism glass type | $d\beta_2/dn_{\it eff}$ @ λ = 1,060 nm | $d\beta_2/dn_{\it eff}$ @ λ = 1,550 nm |
|---|---|---|
| F2 ($n_p$ ≈ 1.6) | 3.82 | 3.85 |
| S-LAL10 ($n_p$ ≈ 1.7) | 2.36 | 2.36 |
| N-SF11 ($n_p$ ≈ 1.75) | 2.09 | 2.1 |

The data of Table 1 indicate that the sensitivity of the highest-index coupling prism 40 at 1,060 nm is about 55% of the sensitivity of the lowest-index coupling prism at 1,550 nm. This can be compensated for by the 3× to 4× greater pixel density of a near-infrared CMOS or CCD camera as compared to IR analog detector 110. The optical resolution at 1,060 nm will be better than at 1,550 nm, since optical resolution scales with wavelength.

Thus, an example system 10 includes: a) light source 60 employing a light-emitting diode operating near 1,060 nm; b) coupling prism 40 with $n_p$≈1.75 and α=60°; c) IR analog detector 110 in the form of a CMOS or CCD camera with pixel spacing in the range 3-8 microns; d) light-scattering element 70 for improving the angular uniformity of illumination, including one incorporated as roughness on coupling prism input surface 42; e) an additional moving light-scattering element 70 for reducing speckle if needed; and e) controller 150 configured to carry out the above-described signal processing.

Such a system 10 with an operating wavelength λ of 1,060 nm can be further simplified by taking advantage of somewhat higher-power (5-7 mW) LEDs available at 1,060 nm. A long-pass filter 66 passing wavelengths above about 1,000 nm or a band-pass filter 66 with bandwidth in the range 20-80 nm can be utilized to limit the bandwidth of the 1,060-nm LED. Moving light-scattering element 70 may be eliminated in this case because the level of speckle is negligible. The scaling argument used to infer the parameters of a working 1,060-nm system works well when changes in background in the collected images due to scattering by substrate 20 can be neglected.

Figure 11A:
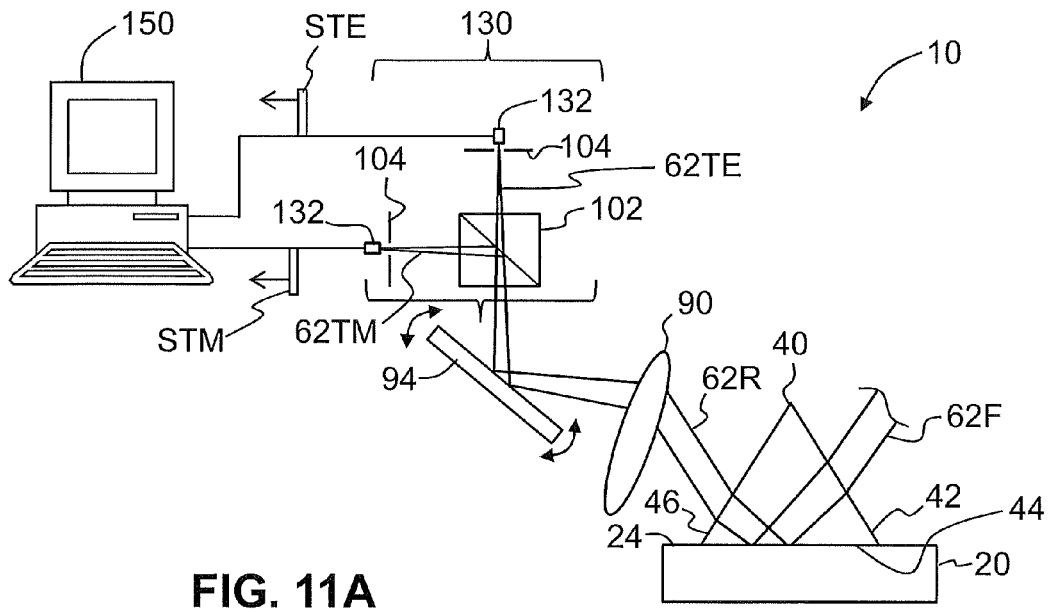
FIGS. 11A and 11B are close-up schematic diagrams of the detector side of the surface-stress measurement system of FIG. 1 and illustrate alternative example embodiments of the photodetector system.

FIG. 11A is a close-up view of a portion of system 10 that illustrates an example embodiment wherein photodetector system 130 includes separate single-pixel photodetectors 132 rather than a single two-dimensional photodetector (camera) 110. This embodiment is a useful alternative to using more expensive long-wavelength two-dimensional photodetectors.

The system 10 of FIG. 11A includes a scanning mirror 94 that directs reflected light 62R from collecting optical system 90 through a polarizing beam-splitting device (PBSD) 102 that separates the TE and TM light components, denoted 62TE and 62TM. The PBSD 102 may be a conventional beam-splitting prism as shown by way of example, or can be another beam-splitting and polarizing device.

The TE and TM light components 62TE and 62TM pass through respective apertures 104 and to respective single-pixel photodetectors 132. The scanning mirror 94 is configured to scan reflected beam 62R, which serves to scan TE and TM light components (beams) 62TE and 62TM past their respective photodetectors 132. The single-pixel photodetectors 132 generate electrical signals STM and STE in response and send these signals to controller 150. In this case the angular reflectance spectrum is related to the temporal dependence of the detected signal.

In FIG. 11A, PBSD 102 is shown schematically as a prism-based beam-splitting device. However, PBSD 102 can comprise any form of polarizing beam-splitting device, and in one example comprises an optical power splitter such as a silicon plate and two polarizers. In an example, a plate of silicon (or other semiconductor material that is transparent at the measurement wavelength) disposed substantially at the Brewster's angle may be used to produce substantially polarized light due to the high reflectivity of Si for s-polarized light at large incidence angles, especially after two reflections at two parallel surfaces. In this case, it is possible to omit the polarizers, although the separated beams may not be propagating in mutually orthogonal directions.

In an example, the semiconductor plate may be wedged by less than 10 degrees, to accommodate a range of angles as used in the measurement. In this way, if some light rays have an incidence angle far from the Brewster angle at the entrance of the plate, it may be closer to Brewster's angle at the exit.

Thus, a significant degree of polarization separation could be obtained over a range of angles of several degrees as needed for the measurement.

The main advantage of this system 10 over a laser-based, sequentially scanning system is the elimination of significant random error due to separate referencing for the TE and TM spectra. In addition, the system of FIG. 11A has the potential to make faster measurements, since the data for the two polarizations are collected simultaneously rather than sequentially.

To ensure proper mapping of the difference in TIR transition on the two detectors 132 onto surface birefringence B and stress, a calibration measurement of one or two calibration samples 20 with known stress levels may be performed first. Using two calibration samples 20 with substantially different levels of stress can help both to precisely correct for a scaling factor due to imperfect positioning of single-pixel photodetectors 132 in the focal planes of the collection lens, and to eliminate any lateral offset of the detectors with respect to their ideal mutual alignment.

In particular, one reference sample 20 may be annealed glass with negligible surface stress, in which case the position of the TIR transition at both single-pixel photodetectors 132 should be identical, or the difference in position should be considered the starting (reference) point for measuring difference in position.

In an alternative embodiment similar to that shown in FIG. 11A, the two single-pixel photodetectors 132 may be disposed on top of each other, such that they would appear co-located in the plane of FIG. 11A, and the arms 62TE and 62TM would appear identical, both going straight or deflected by element 102, which in this case may be a simple mirror. The difference in this embodiment is that reflected light beam 62R, after rotating mirror 94, is separated vertically into two parts which are linearly polarized into TE and TM polarizations as defined by the coupling interface of the prism by corresponding two polarizing elements that are polarized in different directions.

In a similar embodiment, a single linear photodetector is disposed such that the linear array of pixels is stretched orthogonal to the plane of the drawing, and two or more portions of the array are used for detecting TE or TM light prepared corresponding polarizers as described above. This variant is similar to the two-dimensional array described in the embodiment shown in FIG. 1, but in one of the dimensions the set of columns is replaced by temporal scanning. The signal corresponding to a particular moment of time in a TE or TM section of the 1-D array can then be obtained by summing the signals of a chosen subset of pixels in that section at that moment of time. The summed TE and TM signals as a function of time can then be compared to obtain a birefringence estimate using the methods of the three data-processing embodiments described herein. In particular, columns that normally correspond to positions x now correspond to different moments in time t.

In the described scanning embodiments, if the optical path length between the rotating mirror 94 and each of the two detectors is approximately equal to b, while the optical path length from the collecting system or lens 90 to each of the detectors is about f, then the following approximate conversion formula may be used to relate the measured time delay $\Delta t_{TE\text{-}TM}$ between TE and TM signals and a corresponding birefringence:

$$\Delta n_{TE\text{-}TM} \approx \frac{2\omega b}{f \frac{d\beta_2}{dn_{eff}}} \Delta t_{TE\text{-}TM}$$

where $\omega$ is the angular frequency of rotation of the mirror 94 and the sensitivity of exit angle $\beta_2$ to effective index was described earlier.

Figure 11B:
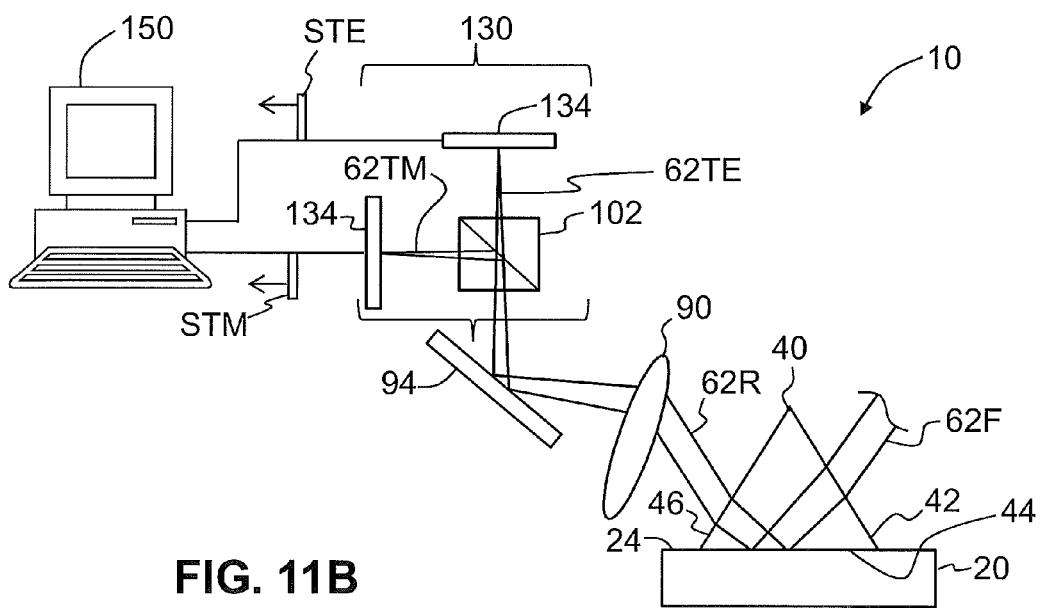

FIG. 11B is similar to FIG. 11A except that single-pixel photodetectors 132 are replaced with linear-array (1×N) or (few pixel×N) photodetectors 134, apertures 104 are removed, and scanning mirror 94 becomes a stationary fold mirror, or may even be omitted if PBSD 102 is placed in its position, and the linear-array photodetectors are placed appropriately along the resulting paths for TE and TM waves. The TE and TM spectra $S_{TE}$ and $S_{TM}$ can then be obtained in a single shot without the need for scanning Now, signals STE and STM include the entire (raw) TE and TM spectra based on a single-line of few-line image rather than on a substantially two-dimensional image.

As with the embodiment of FIG. 11A, taking one or two calibration measurements of one or two samples 20 of known surface birefringence/stress can substantially improve the accuracy of measurements using this embodiment. The PBSD 102 in this embodiment can be in the form of a power splitter and a pair of polarizers, or a high-index (semiconductor) plate or wedge at near-Brewster-angle incidence. In this embodiment, the relationship between transition displacement between the TE- and TM-signal after referencing and the corresponding birefringence is the same as the relationship determined for the system configuration of FIG. 1.

The methods and systems disclosed herein are applicable to some negative-step refractive index profiles with deep regions of negative step, typically greater than $30\lambda/n_s$, as well as to monotonic profiles with smooth continuous change in the refractive index, such as is produced by diffusion. Examples of such profiles include:

$n(z)=n_s+\Delta n*\mathrm{erfc}(z/z_0);$ $n(z)=n_s+\Delta n*\exp(-z/z_0);$ $n(z)=n_s+\Delta n*(1-z/\mathrm{DOL})$ for $z<\mathrm{DOL}$ and $n(z)=n_s$ for $z\geq\mathrm{DOL}$; and with $-0.14<\Delta n/n_s<0$ and $0<z_0<(80)\cdot\lambda/n_s$, or $0<\mathrm{DOL}<(120)\cdot\lambda/n_s$, with z=depth into sample 20 and n(z)=the refractive index profile; $z/z_0$ is a normalized depth coordinate; DOL=depth of layer; and $\Delta n=n_0-n_s$, where $n_0$ is the surface refractive index, i.e., n(0).

For glasses and glass-ceramics having substantial attenuation, the TIR/PR transition is so broadened that conventional measurement systems cannot identify the location of the critical angle $\theta_C$. In an example, system 10 has a measurement error of 5% or less. Yet, the breadth of the TIR/PR transition for, for example, white glass-ceramics is about 30 times larger than this measurement error.

If the complications caused by the scattered light resulting in a non-uniform background in the measured angular spectrum are disregarded, then the broadening of the coupling spectrum is on the order of:

$$\kappa[RIU] = \frac{\alpha_s \lambda}{4\pi} \equiv 1.83 \times 10^{-5} \alpha_s \left[\frac{dB}{mm}\right] \lambda[\mu m]$$

where $\alpha_s$ is the attenuation coefficient usually measured in cm$^{-1}$ or, in the latter version of the formula, in dB/mm. This broadening derives from considering each mode as a harmonic oscillator, where the propagation constant is:

$$\beta = \frac{2\pi}{\lambda}(n_{eff} + i\kappa)$$

Examples of system 10 have a precision of about 1/30 of the typical breadth of a TIR/PR transition. To achieve a measurement standard deviation below σ for the stress-induced surface birefringence B, the breadth of the TIR/PR transition should generally be about 30σ or smaller. Hence, the full width of a typical resonance needs to be 2κ≤30σ.

Hence, the attenuation coefficient in an embodiment of the disclosure is:

$$\alpha[cm^{-1}] \equiv \frac{4\pi\kappa[RIU]}{\lambda[cm]} \leq \frac{60\pi\sigma[RIU]}{\lambda[cm]}$$

$$\alpha[dB/mm] \equiv \frac{\kappa * 10^5}{1.83\lambda[\mu m]} \leq \frac{8.2 \times 10^5 \sigma[RIU]}{\lambda[\mu m]}$$

An example system 10 can measure surface birefringence B with a standard deviation of about 6×10$^{-5}$ at a wavelength of 1.550 microns for a sample 20 whose attenuation α=31 dB/mm. The example system 10 uses a wavelength for which the above criterion for the relationship between attenuation and the required standard deviation of the measured surface birefringence B is met.

A standard deviation of 6.2×10$^{-5}$ RIU was obtained from the measurement results of 12 nominally identical ion-exchanged glass-ceramic samples 20. In addition, obtained was a standard deviation of 5.5×10$^{-5}$ RIU from the measurements of 10 nominally identical samples 20 exchanged in a different bath. In both cases the ion exchange replaced Na ions with Li ions in the surface layer of samples 20. The observed standard deviations reflect not only error due to the imperfections of the measurement equipment but also presumably some minor differences between nominally identical samples 20. It is estimated that accounting for the minor difference between nominally identical samples 20 leads to a criterion where the product αλ may be as high as 80πσ.

In another embodiment, the operating wavelength is selected such that:

$$\alpha[cm^{-1}] \leq \frac{80\pi\sigma[RIU]}{\lambda[cm]}$$

or in dB/mm:

$$\alpha[dB/mm] \leq \frac{1.1 \times 10^6 \sigma[RIU]}{\lambda[\mu m]}$$

In another embodiment, minor improvements in system optics and the data-processing algorithm, and minor decreases in detector noise and optical background noise, lead to the ability to obtain a standard deviation such that αλ may be as high as 130πσ. In that case, the criterion for attenuation selection becomes:

$$\alpha[cm^{-1}] \leq \frac{130\pi\sigma[RIU]}{\lambda[cm]}$$

or in dB/mm:

$$\alpha[dB/mm] \leq \frac{1.8 \times 10^6 \sigma[RIU]}{\lambda[\mu m]}$$

Finally, in some cases the maximum derivative of the reflectivity as a function of angle is substantially larger than the described experimental examples. In such cases the standard deviation could be reduced substantially due to a reduced sensitivity of the measurement to optical and detector noise. In particular, such cases may occur when the attenuation is somewhat lower, and, especially, when the scattering is lower.

Even in a measurement of white glass ceramic with relatively large scattering, a well-optimized system 10 with good suppression of ambient noise and background from scattering achieved a standard deviation of 1.61×10$^{-5}$ RIU as disclosed above. In this case, the product αλ was about 200πσ. In some very well optimized systems that are only limited by broadening due to optical attenuation and where there exists a favorable balance between absorption and scattering, the product αλ may be as high as 250πσ. In an embodiment of the disclosure, the wavelength of operation is chosen such that $$\alpha[cm^{-1}] \leq \frac{250\pi\sigma[RIU]}{\lambda[cm]}$$

or in dB/mm $$\alpha[dB/mm] \leq \frac{3.5 \times 10^6 \sigma[RIU]}{\lambda[\mu m]}$$

As previously mentioned, in an example the optical attenuation of the measured material is generally substantially greater than 1 dB/cm, and in most cases greater than about 1 dB/mm.

An example method includes measuring the attenuation coefficient α as a function of wavelength. This can be accomplished, for example, using very thin plates of the sample material to avoid the regime of diffusion-assisted light propagation. The method then includes plotting α·λ as a function of λ and looking for a wavelength region where α·λ<250 πσ[RIU], 200 πσ[RIU], 130 πσ[RIU], 80πσ[RIU], or 60 πσ[RIU]. Thus, the method includes operating system 10 at a wavelength λ such that the attenuation at that wavelength satisfies one of the above inequalities.

The example system 10 as disclosed herein is intended to characterize surface birefringence B of samples 20 that have an attenuation α in the range from about 1 dB/mm to about 105 dB/mm in the near infrared, and to above 120 dB/mm in the visible. The samples 20 may have attenuation above 105 dB/mm in some regions of the infrared where measurements are not to be performed, with the exception of the very near infrared, 800-1,100 nm, where measurements of some samples may be possible even at attenuation levels up to about 180 dB/mm.

System 10 can have different configurations besides that shown by way of example in FIG. 1. Some of the steps for processing the angular spectra may need to be altered to accommodate the different configurations. For example, row summation may depend on the particular configuration and whether the photodetector system 130 is one or two-dimensional.

In particular embodiments of system 10, the relationship between variation of exit angle and variation in effective index of the corresponding propagation mode of the substrate may be different. However, this does not affect the data processing, but only the equation for converting pixel spacing to birefringence.

Therefore, a general embodiment of the disclosure is directed to processing the raw data representing reflected intensity as a function of pixel, angle, or time (in the case of scanning system) available for two different polarization states. The appropriate data processing algorithm as described above is then applied to obtain a value of surface birefringence or stress.

The raw data come with a system-specific formula relating pixel/column separation, angular separation, or temporal separation, with refractive index change or birefringence. The data processing steps for obtaining precise estimate of birefringence are independent of the applied formula.

Figure 12A:
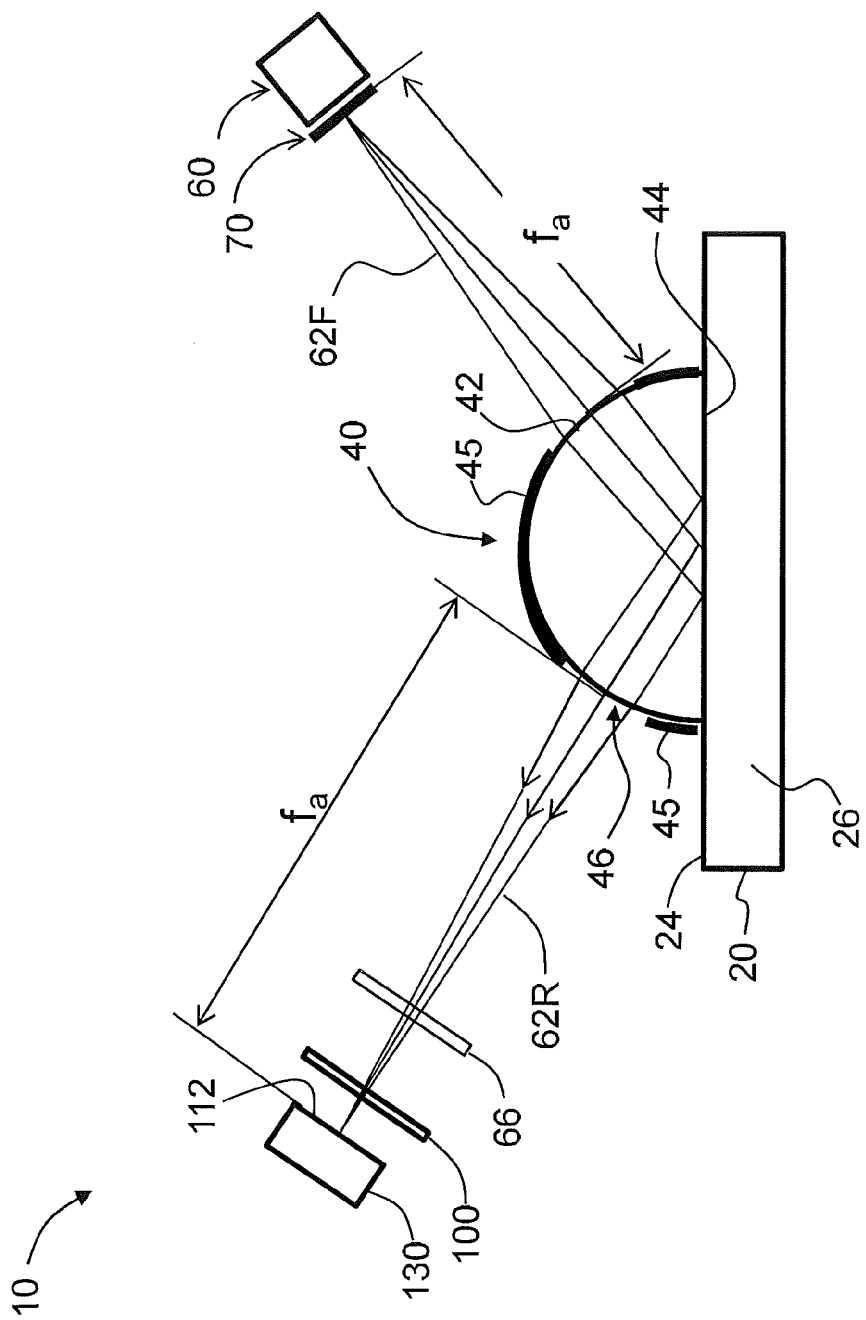
FIGS. 12A through 12C are schematic diagrams of alternate example embodiments of the surface-stress measurement system according to the disclosure, wherein the coupling prism has a curved surface.

FIG. 12A is an example embodiment of system 10 wherein coupling prism 40 has curved surface. The curved portion of the prism surface can be represented geometrically in one example as part of a cylindrical surface that defines input and output surfaces 42 and 46. The curved surfaces 42 and 46 constitute a portion of or the entirety of focusing and collecting optical systems 80 and 90, respectively.

The focal length of the curved surface on the air side $f_a$ is given by the equation:

$$f_a = \frac{R}{n_p - 1}$$

where R is the radius of curvature of the cylindrical surface. Photodetector system 130 is positioned along the optical path approximately a distance $f_a$ from curved output surface 46.

In an alternative embodiment, coupling prism 40 is hemispherical. In yet another embodiment, a stand-alone focusing lens 80 may be inserted between the light source 60 and the curved coupling prism 40, or a stand-alone collecting lens 90 may be inserted between the curved prism and the photodetector system 130, or both. In such a configuration, the distance between the light source 60 and coupling prism 40 may need to be changed for optimum illumination. In addition, the distance between coupling prism 40 and photodetector system 130 may need to be changed such that plane waves propagating inside the coupling prism are focused into lines or dots at photodetector system 130. Light-blocking elements 45 may be employed to define more openings for passing light focused light 62F and reflected light 62R.

In FIG. 12A, light source 60 illuminates light-scattering element 70, such as a diffuser, which is desirably strongly scattering at the operating wavelength λ. Light-scattering member 70 is substantially a distance $f_a$ from curved input surface 42 of coupling prism 40. System 10 of FIG. 12A may have a reduced optical resolution than that of system 10 of FIG. 1 due to more significant spherical and other aberrations that can rise from the curved surfaces of coupling prism 40. However, it can perform comparably well when used for measurements of samples 20 having a large amount of attenuation, where the transition of reflectivity around the critical angle is significantly broader than for low-attenuation samples. In an example, the radius of curvature R of curved coupling prism 40 is about 40 mm, $n_p$ is about 1.6, the refractive index of the substrate is $n_s=1.536$, and the focal length $f_a$ is thus about 33.3 mm.

In the embodiment of FIG. 12A, the relationship between spatial shift of critical angle $\Delta x$ and corresponding birefringence $\Delta n_{TE-TM}$ is simpler than in the case of system 10 of FIG. 1, and is given by the expression:

$$\frac{\Delta n_{TE-TM}}{\Delta x} = \frac{dn_{eff}}{d\theta}\frac{d\theta}{dx} \approx n_p \cos\theta \frac{1}{f_a} = \sqrt{n_p^2 - n_{eff}^2}\frac{n_p - 1}{R}$$

When the variation in $n_{eff}$ over the range of angles involved in the measurement in the vicinity of the critical angle is significantly smaller than the difference between $n_p$ and $n_{eff}$, the average $n_{eff}^{av}$ value for $n_{eff}$ can be used to convert the shift of the TIR transition to measurement of birefringence:

$$\Delta n_{TE-TM} = \Delta x \sqrt{n_p^2 - n_{eff}^{av2}}\frac{n_p - 1}{R}$$

In an example, if the refractive index change introduced by stress or in general by the ion exchange is significantly smaller than the difference $n_p - n_s$, the substrate index $n_s$ can be substituted for the average effective index:

$$\Delta n_{TE-TM} = \Delta x \sqrt{n_p^2 - n_s^2}\frac{n_p - 1}{R}$$

Alternatively, the average incidence angle $\theta_{av}$ or the approximate estimate of critical angle may be used:

$$\Delta n_{TE-TM} = \Delta x \cos\theta_{av}\frac{n_p - 1}{R}$$

The angular sensitivity $d\theta/dn_{eff}$ is comparable to the angular sensitivity $d\beta_2/dn_{eff}$ for the embodiment of system 10 of FIG. 1. The relatively short focal length of curved coupling prisms of moderate size means that the sensitivity of linear shift $\Delta x$ to shift in effective index may be several times smaller than that of system 10 of FIG. 1 with example focal length f=75 mm.

Figure 12B:
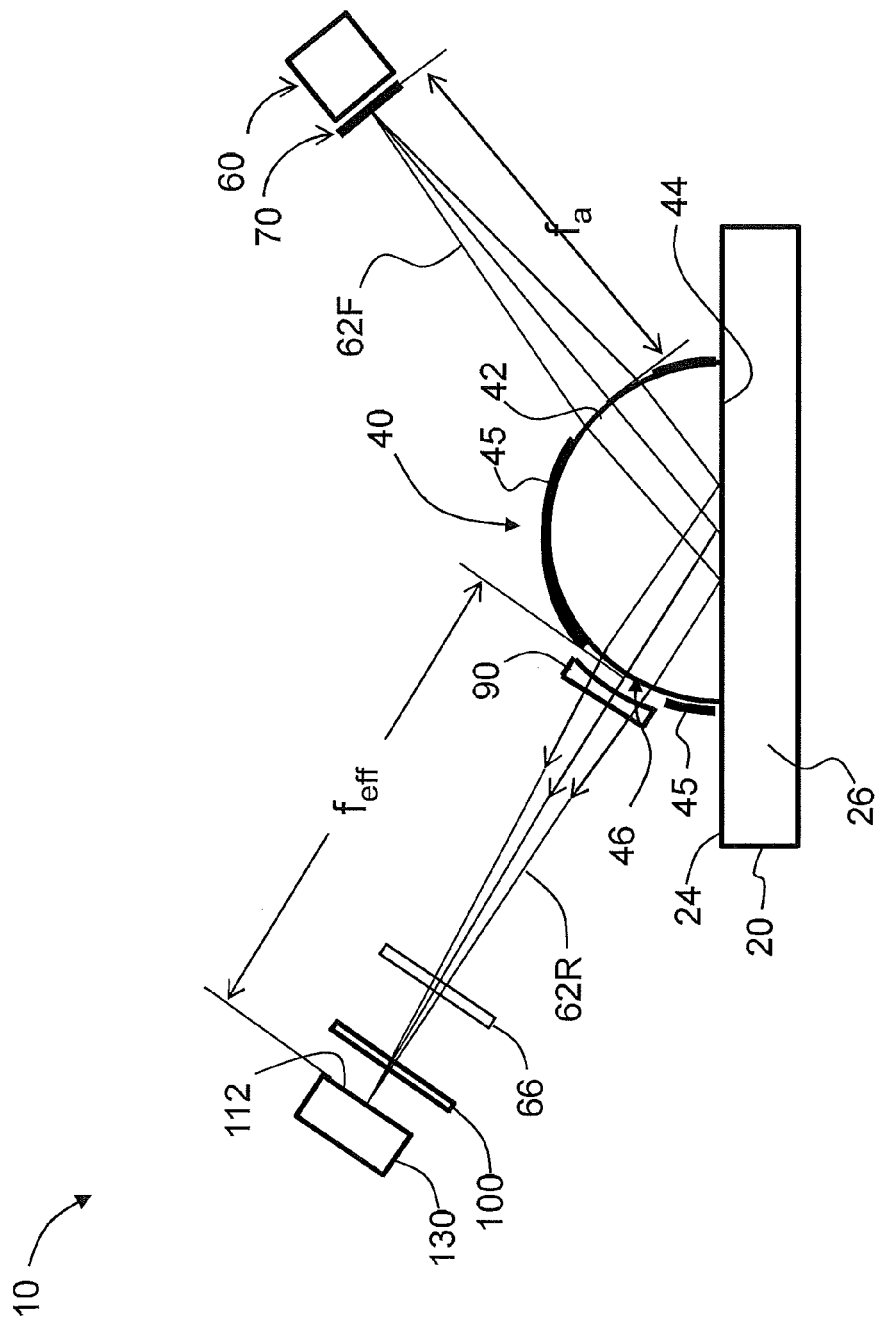

With reference to FIG. 12B, to increase the sensitivity, it is desirably to employ collection lens 90 adjacent output surface 46 of coupling prism 40. In an example, collection lens 90 has negative optical power, such as a plano-concave, double-concave, or negative-meniscus lens. A negative-power collection lens 90 serves to increase the effective focal length of the combined system containing the curved output surface 46 and the attached or stand-alone collection lens 90.

In this case, photosensitive surface 112 of photodetector system 130 is positioned at the focal plane of the combined system with effective focal length $f_{eff}$ as shown in FIG. 12B. In particular, when lens 90 is attached or in very close proximity to exit surface 46, the overall effective focal length $f_{eff}$ can be found by $$\frac{1}{f_{eff}} \approx \frac{1}{f_a} + \frac{1}{f_l}$$

where $f_l$ is the focal length of the negative collection lens 90, which has a negative value in the above equation, resulting in $f_{eff} > f_a$.

The sensor plane 112 of the detector is thus positioned a distance approximately $f_{eff}$ from the thin negative collection lens 90 that is located proximate to output surface 46. In an example, R=15 mm and $n_p$=1.6, such that $f_a$=25 mm, and $f_l$=−30 mm. This results in an effective focal length $f_{eff}$ of 150 mm, and $$\frac{\Delta n_{TE-TM}}{\Delta x} \approx \frac{\sqrt{n_p^2 - n_s^2}}{f_{eff}}$$

$$= \sqrt{n_p^2 - n_s^2} \left( \frac{n_p - 1}{R} + \frac{1}{f_l} \right)$$

$$= \sqrt{n_p^2 - n_s^2} \left( \frac{n_p - 1}{R} - \frac{1}{|f_l|} \right)$$

evaluating at $2.99 \times 10^{-6}$ RIU/μm. If the effective sensor pixel size is 19.8 μm, then the birefringence resolution corresponding to 1 pixel is:

$$\delta n_{pix} = 5.9 \times 10^{-5} \text{ RIU/pix}$$

Figure 12C:
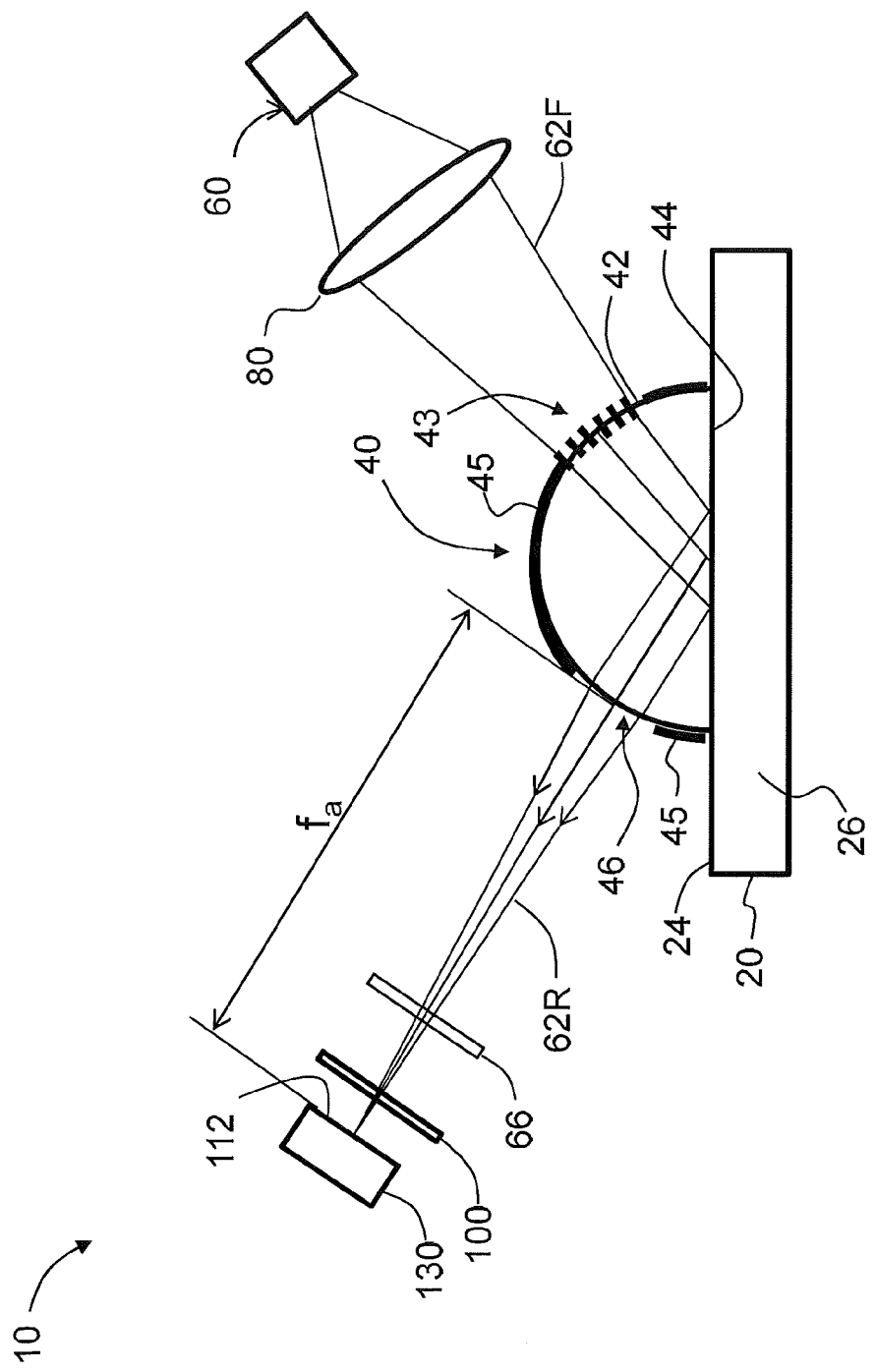

FIG. 12C shows an example embodiment of system 10 similar to FIG. 12A, but with scattering element 43 incorporated into input surface 42. This embodiment can serve to provide a more uniform angular distribution of illumination.

Another alternative embodiment may be obtained by combining the embodiments of FIG. 12B and FIG. 12C, where scattering element 43 is incorporated on input surface 42, and collection lens 90 is added near the output surface 46 for increasing linear sensitivity $\Delta x/\Delta n_{eff}$ by increasing the effective focal length.

Different embodiments of system 10 can be formed by combining features of the systems of FIG. 1 and FIGS. 12A through 12C. For example, input surface 42 of coupling prism 40 may be curved (e.g., cylindrical, ellipsoidal, or spherical), while the output surface 46 may be flat. In such cases, the equations relevant to FIG. 1 describe the relationship between birefringence B on the one hand, and pixel or angular separation, on the other.

In another example, input surface 42 of coupling prism 40 is flat, with or without scattering surface 43, while output surface 46 is curved.

It will be apparent to those skilled in the art that various modifications to the preferred embodiments of the disclosure as described herein can be made without departing from the spirit or scope of the disclosure as defined in the appended claims. Thus, the disclosure covers the modifications and variations, provided they come within the scope of the appended claims and the equivalents thereto.

What is claimed is:

1. A method of optically measuring an amount of birefringence B in a surface of a sample, comprising:
    a) digitally capturing TE and TM angular spectra of intensity versus pixel number for the sample, wherein the digital capturing is defined by pixels having an index resolution;
    b) processing the TE and TM angular spectra to minimize differences between respective regions of the TE and TM angular spectra, wherein the respective regions include a rate of change of intensity with angle that is at least 40% of a maximum rate of change of intensity with angle;
    c) determining an amount of shift in pixels that best overlaps the processed TE and TM spectra; and
    d) determining the amount of birefringence B by multiplying the pixel shift by the index resolution.

2. The method of claim 1, wherein said rate of change is at least 70% of the maximum rate of change.

3. The method of claim 1, further including capturing multiple TE- and TM-spectrum images and averaging the multiple images to reduce speckle.

4. The method of claim 3, wherein the digital capturing of the TE and TM angular spectra is performed so that either:
    a) the TE and TM angular spectra are simultaneously captured as TE and TM images on respective TE and TM sections of a photodetector; or
    b) the TE and TM angular spectra are sequentially captured as TE and TM images on one or more photodetectors.

5. The method of claim 4, wherein the photodetector comprises an infrared analog detector that captures TE and TM images, and wherein said digital capturing includes processing the TE and TM images with a frame grabber.

6. The method of claim 1, wherein the digitally captured TE and TM spectra constitute raw TE and TM spectra, and further comprising:
    capturing reference TE and TM angular spectra in the absence of the sample;
    normalizing the raw TE and TM angular spectra by the reference TE and TM angular spectra; and
    processing the normalized TE and TM angular spectra per acts b) through d).

7. The method of claim 6, further comprising correcting for a nonlinear detector response to obtain normalized TE and TM angular spectra.

8. The method of claim 1, wherein the sample has a stress-optic coefficient SOC and further comprising:
    calculating an amount of surface stress σ from the birefringence B via the relationship σ=B·SOC.

9. The method of claim 1, wherein the digital capturing includes receiving the TE and TM spectra on separate photodetectors.

10. The method of claim 1, wherein the digital capturing includes scanning the TE and TM spectra past either:
    a) two single photodiodes; or
    b) a linear array of photo-sensing elements.

11. The method of claim 1, further comprising:
    directing light from a light source to a coupling prism that is optically coupled to a top surface of the sample.

12. The method of claim 11, further comprising passing the light through at least one light-scattering element disposed between the light source and a coupling surface of the coupling prism.

13. The method of claim 1, wherein processing the TE and TM angular spectra includes:
    summing multiple TE spectra to obtain a summed TE spectrum;
    summing multiple TM spectra to obtain a summed TM spectrum;
    low-pass filtering the summed TE and TM spectra;
    band-pass filtering the low-pass-filtered summed TE and TM spectra; and
    normalizing the band-pass-filtered and low-pass-filtered TE and TM spectra so that each of the TE and TM spectra has a range from 0 to 1.

14. The method of claim 1, wherein the sample comprises a glass or a glass ceramic having an attenuation $\alpha_s$, wherein the birefringence has measurement error σ, and wherein the operating wavelength is an infrared wavelength that satisfies the condition $\alpha_s\lambda<250\pi\sigma$.

15. A method of optically measuring an amount of birefringence B in a surface of a sample made of ion-exchanged glass or a glass-ceramic, comprising:
  a) digitally capturing TE and TM angular spectra of intensity versus pixel number for the sample, wherein the digital capturing is defined by pixels having an index resolution;
  b) optionally normalizing the TE and TM angular spectra to a total-reflectivity spectrum obtained without sample, representative of an angular distribution of an illumination system;
  c) processing the TE and TM angular spectra or the optionally normalized TE and TM angular spectra to obtain filtered TE and TM spectra;
  d) calculating respective derivatives of the filtered TE and TM spectra;
  e) determining the angular locations of respective maxima of the respective derivatives; and
  f) determining the shift by the angular separation of the respective derivative maxima.

16. A system for optically measuring an amount of birefringence B in a surface of a sample made of ion-exchanged glass or a glass-ceramic, comprising:
  a prism optically coupled to the sample surface at a coupling surface and having an input surface and an output surface;
  a light source that emits light having an operating wavelength in the infrared range, with the light source optically coupled to the prism coupling surface via the input surface and over a first optical path;
  a photodetector system optically coupled to the prism coupling surface via the output surface over a second optical path and configured to receive TE and TM light representative of TE and TM angular spectra of the sample, wherein the photodetector system includes one or more pixels having an index resolution; and
  a controller electrically connected to the photodetector system and arranged to receive the TE and TM images, the controller being configured with instructions embodied in a computer-readable medium to process the TE and TM images to minimize differences between respective regions of the TE and TM angular spectra, wherein the respective regions include a rate of change of intensity with angle that is at least 40% of a maximum rate of change of intensity with angle, to determine an amount of pixel shift that best overlaps the processed TE and TM spectra in the respective regions and the amount of birefringence B by multiplying the pixel shift by the index resolution.

17. The system of claim 16, where said rate of change of intensity with angle is at least 70%.

18. The system of claim 16, wherein the photodetector system comprises an IR analog detector electrically connected to a frame grabber, and wherein a TE/TM polarizer is disposed in front of the IR analog detector, the TE/TM polarizer including at least one TE section and at least one TM section that defines corresponding at least one TE region and at least one TM region of the IR analog detector.

19. The system of claim 16, wherein the sample has an attenuation $\alpha_s$, the system has a birefringence measurement error σ, and wherein the operating wavelength is an infrared wavelength that satisfies the condition $\alpha_s\lambda<250\pi\sigma$.

20. The system of claim 16, further comprising at least one light-scattering element disposed between the light source and the prism coupling surface.

21. The system of claim 16, wherein the photodetector system includes either:
  a) first and second single-pixel detectors optically separated by a polarizing beam-splitting device disposed in the second optical path; or
  b) first and second linear detectors optically separated by a polarizing beam-splitting device disposed in the second optical path; or
  c) one linear detector having a TM section and a TE section optically separated by a polarizing beam-splitting device disposed in the second optical path.

* * * * *